(12) United States Patent
Yamano et al.

(10) Patent No.: US 8,691,718 B2
(45) Date of Patent: Apr. 8, 2014

(54) DIPHOSPHINE LIGAND AND TRANSITION METAL COMPLEX USING THE SAME

(75) Inventors: Mitsuhisa Yamano, Osaka (JP); Mitsutaka Goto, Osaka (JP); Shinji Kawaguchi, Osaka (JP); Masatoshi Yamada, Osaka (JP); Jun-ichi Kawakami, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 757 days.

(21) Appl. No.: 11/992,167

(22) PCT Filed: Sep. 20, 2006

(86) PCT No.: PCT/JP2006/319095
§ 371 (c)(1),
(2), (4) Date: Mar. 18, 2008

(87) PCT Pub. No.: WO2007/034975
PCT Pub. Date: Mar. 29, 2007

(65) Prior Publication Data
US 2009/0270635 A1 Oct. 29, 2009

(30) Foreign Application Priority Data
Sep. 20, 2005 (JP) ................................. 2005-272599

(51) Int. Cl.
*B01J 31/24* (2006.01)
*C07F 15/00* (2006.01)
*C07F 1/08* (2006.01)

(52) U.S. Cl.
CPC ......... *B01J 31/2452* (2013.01); *C07F 15/0053* (2013.01); *C07F 15/0066* (2013.01); *C07F 15/008* (2013.01); *C07F 15/004* (2013.01)
USPC .............. 502/208; 502/213; 548/413; 564/15

(58) Field of Classification Search
CPC .............. B01J 31/2452; C07F 15/0053; C07F 15/0066; C07F 15/008; C07F 15/004
USPC ...................... 502/213, 208; 548/413; 564/15
See application file for complete search history.

(56) References Cited

U.S. PATENT DOCUMENTS

| 5,159,093 | A | 10/1992 | Taketomi et al. |
| 7,208,633 | B2 * | 4/2007 | Goto et al. ...................... 568/17 |
| 2005/0027124 | A1 | 2/2005 | Goto et al. |

FOREIGN PATENT DOCUMENTS

| GB | 2 351 735 | | 1/2001 |
| JP | 09124669 | A * | 5/1997 |
| JP | 11-310561 | | 11/1999 |
| JP | 2003/231691 | | 8/2003 |
| WO | 02/40491 | | 5/2002 |

OTHER PUBLICATIONS

Machine translation of JP 09124669 A by Sayo et al., obtained from http://dossier1.ipdl.inpit.go.jp/AIPN/odse_top_fwi.ipdl?N0000=7401 on Jun. 10, 2013.*

(Continued)

*Primary Examiner* — Joseph Kosack
*Assistant Examiner* — Matthew Coughlin
(74) *Attorney, Agent, or Firm* — Wenderoth, Lind & Ponack, L.L.P.

(57) ABSTRACT

The present invention provides a novel ligand represented by the following formula and a novel transition metal complex having the ligand, which shows superior enantioselectivity and catalytic efficiency, particularly high catalyst activity, in various asymmetric synthesis reactions.
A transition metal complex having, as a ligand, a compound represented by the formula

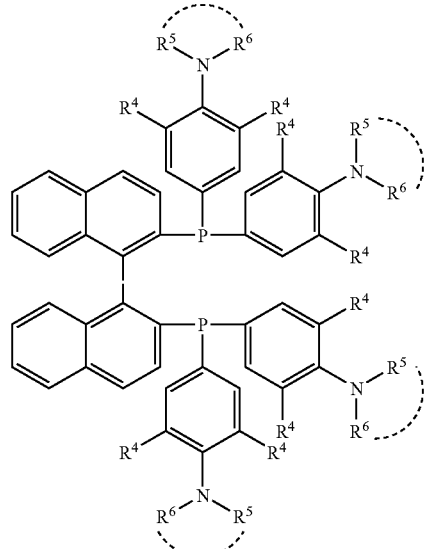

wherein $R^4$ is a hydrogen atom or a $C_{1-6}$ alkyl group optionally having substituent(s), and $R^5$ and $R^6$ are each a $C_{1-6}$ alkyl group optionally having substituent(s), or the formula

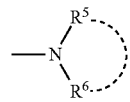

is a group represented by the formula

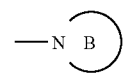

wherein ring B is a 3- to 8-membered ring optionally having substituent(s).

7 Claims, No Drawings

(56) References Cited

OTHER PUBLICATIONS

International Search Report issued Dec. 12, 2006 in the International (PCT) Application of which the present application is the U.S. National Stage.

D. G. Genov et al., "Asymmetric Hydrogenation of Ketones Catalyzed by $Ru^{II}$-bicp Complexes", Angew. Chem. Int. Ed., vol. 43, pp. 2816-2819, 2004.

European Search Report dated Dec. 23, 2011 in corresponding European Application No. 11 18 9532.

Kasumov, V.T., et al., "Synthesis and ESR studies of redox reactivity of bis (3,5-di-*tert*-butyl-1,2-benzoquinone-2-monooximato)Cu(II)", Spectrochimica Acta Part A, vol. 56, 2000, pp. 841-850.

* cited by examiner

DIPHOSPHINE LIGAND AND TRANSITION METAL COMPLEX USING THE SAME

This application is a U.S. national stage of International Application No. PCT/JP2006/319095 filed Sep. 20, 2006.

TECHNICAL FIELD

The present invention relates to a novel ligand, a transition metal complex having the novel ligand, and an asymmetric synthesis reaction using the transition metal complex.

BACKGROUND ART

Known asymmetric synthesis reaction includes asymmetric reductions, asymmetric isomerizations, asymmetric hydrosilylations and the like, and transition metal complexes with rhodium, ruthenium, iridium and the like having an optically active compound as a ligand are mainly used. Conventionally, 2,2'-bis(diphenylphosphino)-1,1'-binaphthyl (hereinafter sometimes to be also abbreviated as BINAP) is generally used as an optically active phosphine. However, since the reactivity, steric selectivity, catalytic efficiency and the like of BINAP depend on the substrate and are not always sufficient, various other optically active phosphines have been produced and reported (e.g., Handbook of Enantioselective Catalysis with Transition Metal Compounds, published by VCH Verlag GmbH, 1993). Of the optically active phosphines, optically active phosphines having a dialkylamino group as a substituent are described in WO03/048174 and WO02/040491.

Of the compounds having a 1,1'-binaphthyl skeleton like BINAP, for example, JP-A-61-63690 describes that a ruthenium complex having 2,2'-bis(di(p-tolyl)phosphino)-1,1'-binaphthyl as a ligand is useful for the asymmetric reduction of a carbon-carbon double bond. JP-A-3-255090 describes that a ruthenium complex having 2,2'-bis(bis(3,5-dialkylphenyl)phosphino)-1,1'-binaphthyl as a ligand is useful for the asymmetric reduction of β-ketoester and JP-A-2004-196793 describes that a ruthenium complex having 2,2'-bis(bis(3,5-di-tert-butyl-4-methoxyphenyl)phosphino)-1,1'-binaphthyl as a ligand is useful therefor.

However, enantioselectivity or catalytic efficiency may be insufficient depending on the reaction substrate in the reactions using these transition metal catalysts.

DISCLOSURE OF THE INVENTION

The present invention provides a novel ligand and a novel transition metal complex having the ligand, which shows superior enantioselectivity and catalytic efficiency, particularly high catalyst activity, in various asymmetric synthesis reactions.

The present inventors have found that a compound represented by the formula

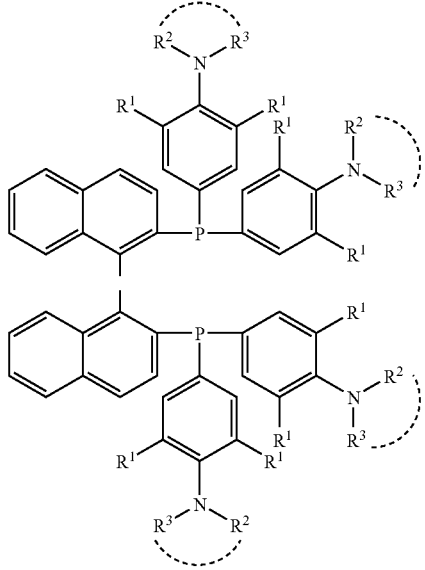

wherein $R^1$ is a hydrogen atom or a $C_{1-6}$ alkyl group optionally having substituent(s), and $R^2$ and $R^3$ are each a $C_{1-6}$ alkyl group optionally having substituent(s), or the formula

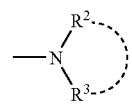

is a group represented by the formula

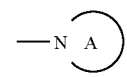

wherein ring A is a 3- to 8-membered ring optionally having substituent(s), provided that 2,2'-bis[bis(4-dimethylaminophenyl)phosphino]-1,1'-binaphthyl is excluded (hereinafter to be abbreviated as compound (I)), or a salt thereof is useful as a novel ligand, and that a transition metal complex having a compound encompassing compound (I), which is represented by the formula

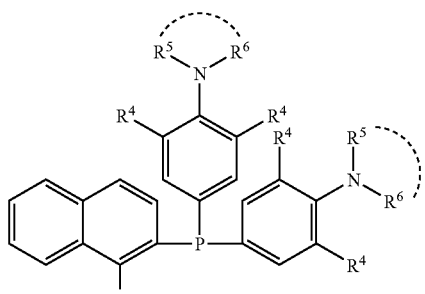

-continued

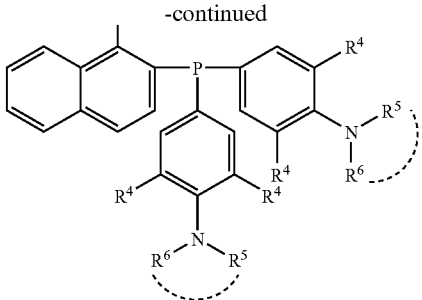

wherein $R^4$ is a hydrogen atom or a $C_{1-6}$ alkyl group optionally having substituent(s), and $R^5$ and $R^6$ are each a $C_{1-6}$ alkyl group optionally having substituent(s), or the formula

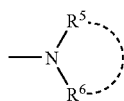

is a group represented by the formula

wherein ring B is a 3- to 8-membered ring optionally having substituent(s) (hereinafter to be abbreviated as compound (II)) as a ligand shows superior enantioselectivity and particularly, catalytic efficiency in asymmetric synthesis reactions, particularly asymmetric reduction reactions, upon which the present invention is based.

Accordingly, the present invention relates to

[1] a compound represented by the formula

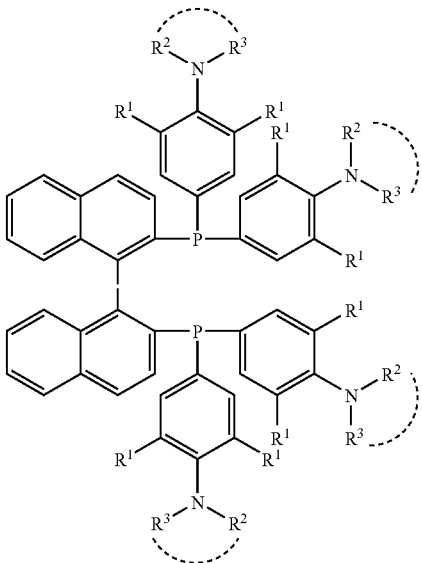

wherein $R^1$ is a hydrogen atom or a $C_{1-6}$ alkyl group optionally having substituent(s), and $R^2$ and $R^3$ are each a $C_{1-6}$ alkyl group optionally having substituent(s), or the formula

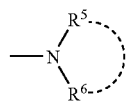

is a group represented by the formula

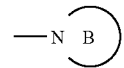

wherein ring A is a 3- to 8-membered ring optionally having substituent(s), provided that 2,2'-bis[bis(4-dimethylaminophenyl)phosphino]-1,1'-binaphthyl is excluded, or a salt thereof,

[2] the compound of [1], wherein $R^1$, $R^2$ and $R^3$ are each a $C_{1-6}$ alkyl group optionally having substituent(s),

[3] the compound of [1], wherein $R^1$, $R^2$ and $R^3$ are each an unsubstituted $C_{1-6}$ alkyl group,

[4] the compound of [1], which is 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl or 2,2'-bis[bis(4-dimethylamino-3,5-diisopropylphenyl)phosphino]-1,1'-binaphthyl,

[5] the compound of any of [1] to [4], which is an optically active compound,

[6] a transition metal complex having, as a ligand, a compound represented by the formula

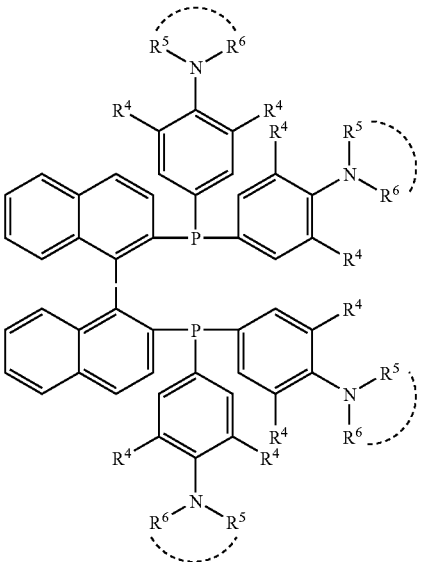

wherein $R^4$ is a hydrogen atom or a $C_{1-6}$ alkyl group optionally having substituent(s), and $R^5$ and $R^6$ are each a $C_{1-6}$ alkyl group optionally having substituent(s), or the formula

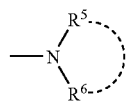

is a group represented by the formula

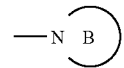

wherein ring B is a 3- to 8-membered ring optionally having substituent(s),

[7] the transition metal complex of [6], wherein the transition metal is rhodium, ruthenium, iridium, palladium, nickel or copper,

[8] the transition metal complex of [6], wherein the transition metal is rhodium, ruthenium or palladium,
[9] the transition metal complex of [6], wherein $R^4$ is a hydrogen atom or an unsubstituted $C_{1-6}$ alkyl group, and $R^5$ and $R^6$ are each an unsubstituted $C_{1-6}$ alkyl group,
[10] the transition metal complex of [6], which is selected from the following:
(1) [Ru(OAc)$_2$(L)];
(2) [RuCl$_2$(L)(dmf)$_n$];
(3) [RuCl(Ar)(L)]Cl;
(4) [Ru(2-methylallyl)$_2$(L)];
(5) [RuCl$_2$(L)(X)];
(6) (NH$_2$Et$_2$)[{RuCl(L)}$_2$(μ-Cl)$_3$];
(7) [Rh(Y)(L)]Z;
(8) [PdCl$_2$(L)]; and
(9) [{Pd(L)}$_2$(μ-OH)$_2$]Z$_2$
wherein L is 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl or 2,2'-bis[bis[4-(pyrrolidin-1-yl)phenyl]phosphino]-1,1'-binaphthyl, Ac is acetyl, dmf is N,N-dimethylformamide, n is an integer of not less than 1, Ar is benzene optionally having substituent(s), 2-methylallyl is η$^3$-2-methylallyl, X is ethylenediamine, 1,2-diphenylethylenediamine or 1,1-di(4-anisyl)-2-isopropyl-1,2-ethylenediamine, Y is 1,5-cyclooctadiene or norbornadiene, Z is a counter anion and trifluoromethanesulfonate, tetrafluoroborate, perchlorate, hexafluorophosphate or tetraphenylborate,
[11] a catalyst comprising the transition metal complex of [6],
[12] a compound represented by the formula

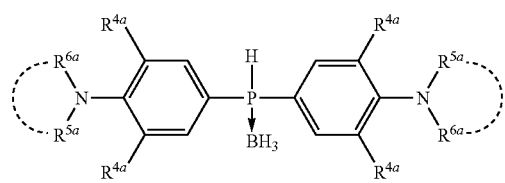

wherein $R^{4a}$ is a hydrogen atom or a $C_{1-6}$ alkyl group optionally having substituent(s), and $R^{5a}$ and $R^{6a}$ are each a $C_{1-6}$ alkyl group optionally having substituent(s), or the formula

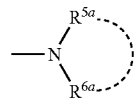

is a group represented by the formula

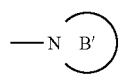

wherein ring B' is a 3- to 8-membered ring optionally having substituent(s), provided that bis(4-dimethylaminophenyl)phosphine-borane complex is excluded, or a salt thereof, and
[13] the compound of [12], wherein $R^{4a}$, $R^{5a}$ and $R^{6a}$ are each a $C_{1-6}$ alkyl group optionally having substituent(s).

In addition, the present invention relates to
[14] a method for producing a compound represented by the formula

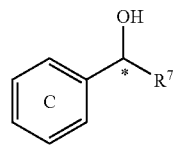

wherein ring C is a benzene ring optionally having substituent(s), $R^7$ is a $C_{1-6}$ alkyl group optionally having substituent(s), and * shows the position of an asymmetric carbon, or a salt thereof, which comprises subjecting a compound represented by the formula

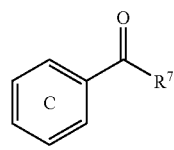

wherein each symbol is as defined above, or a salt thereof to a reduction reaction in the presence of the transition metal complex of [6],
[15] a method for producing a compound represented by the formula

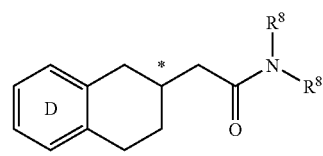

wherein ring D is a benzene ring optionally having substituent(s), $R^8$ is a $C_{1-6}$ alkyl group optionally having substituent(s), and * shows the position of an asymmetric carbon, or a salt thereof, which comprises subjecting a compound represented by the formula

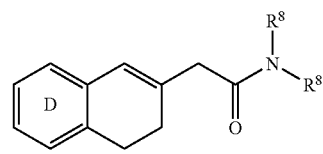

wherein each symbol is as defined above, or a salt thereof, to a reduction reaction in the presence of the transition metal complex of [6],
[16] a method for producing a compound represented by the formula

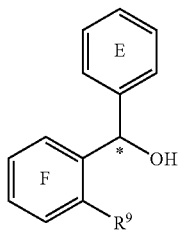

wherein ring E and ring F are each a benzene ring optionally having substituent(s), $R^9$ is an amino group optionally having substituent(s), and * shows the position of an asymmetric carbon, or a salt thereof, which comprises subjecting a compound represented by the formula

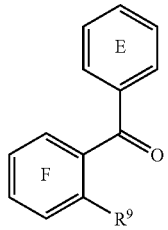

wherein each symbol is as defined above, or a salt thereof, to a reduction reaction in the presence of the transition metal complex of [6], and the like.

BEST MODE FOR EMBODYING THE INVENTION

Compound (I) and compound (II) include an (R) form, an (S) form and a mixture of an (R) form and an (S) form (no limitation on the ratio of the two), with preference given to an optically active form.

The definitions of the substituents of compound (I) and compound (II) are shown in the following.

The "$C_{1-6}$ alkyl group" of the "$C_{1-6}$ alkyl group optionally having substituent(s)" for $R^1$, $R^2$, $R^3$, $R^4$, $R^5$ or $R^6$ is, for example, methyl, ethyl, propyl, isopropyl, butyl, isobutyl, sec-butyl, tert-butyl, pentyl, hexyl and the like.

The "substituent" of the "$C_{1-6}$ alkyl group optionally having substituent(s)" for $R^1$, $R^2$, $R^3$, $R^4$, $R^5$ or $R^6$ is, for example, a halogen atom (e.g., fluorine atom, chlorine atom, bromine atom, iodine atom), nitro, nitroso, cyano, hydroxy, $C_{1-6}$ alkoxy group (e.g., methoxy, ethoxy, propoxy, isopropoxy, butoxy, isobutoxy, sec-butoxy, tert-butoxy, pentoxy, hexyloxy and the like), formyl, $C_{1-6}$ alkyl-carbonyl group (e.g., acetyl, propionyl, butyryl, isobutyryl, valeryl, isovaleryl, pivaloyl and the like), $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like), carboxyl, N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), N,N-di-$C_{1-6}$ alkylcarbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl and the like) and the like. One to three selected from these substituents may be present at substitutable position(s).

$R^1$ is preferably a hydrogen atom or an unsubstituted $C_{1-6}$ alkyl group, particularly preferably a hydrogen atom, methyl, ethyl, isopropyl and the like.

$R^2$ and $R^3$ are preferably a $C_{1-6}$ alkyl group optionally having substituent(s), more preferably an unsubstituted $C_{1-6}$ alkyl group, particularly preferably methyl, ethyl and the like.

$R^4$ is preferably a hydrogen atom or an unsubstituted $C_{1-6}$ alkyl group, particularly preferably a hydrogen atom, methyl, ethyl, isopropyl and the like.

$R^5$ and $R^6$ are preferably a $C_{1-6}$ alkyl group optionally having substituent(s), more preferably an unsubstituted $C_{1-6}$ alkyl group, particularly preferably methyl, ethyl and the like.

In addition, ring A and ring B represented by the formula

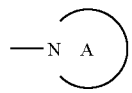

wherein ring A is a 3- to 8-membered ring optionally having substituent(s) and the formula

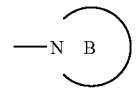

wherein ring B is a 3- to 8-membered ring optionally having substituent(s) are, for example, the following cyclic groups.

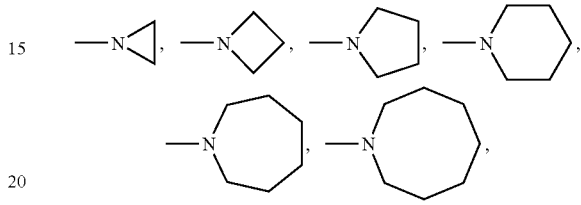

These cyclic groups may have substituent(s), and examples of the substituent include nitro, nitroso, cyano, hydroxy, $C_{1-6}$ alkoxy group (e.g., methoxy, ethoxy, propoxy, isopropoxy, butoxy, isobutoxy, sec-butoxy, tert-butoxy, pentoxy, hexyloxy and the like), formyl, $C_{1-6}$ alkyl-carbonyl group (e.g., acetyl, propionyl, butyryl, isobutyryl, valeryl, isovaleryl, pivaloyl and the like), $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like), carboxyl, N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), N,N-di-$C_{1-6}$ alkylcarbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl and the like) and the like. One to three selected from these substituents may be present at substitutable position(s).

As ring A and ring B,

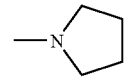

is particularly preferable.

As compound (I), one wherein $R^1$, $R^2$ and $R^3$ are each a $C_{1-6}$ alkyl group optionally having substituent(s) is preferable, and one wherein $R^1$, $R^2$ and $R^3$ are each an unsubstituted $C_{1-6}$ alkyl group is more preferable. In addition, one wherein $R^1$ is a hydrogen atom, and $R^2$ and $R^3$ are each unsubstituted ethyl, or

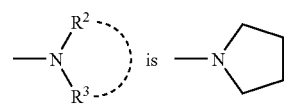

is also preferable.

Preferably, compound (I) is specifically 2,2'-bis[bis(4-dimethylamino-3,5-dimethylphenyl)phosphino]-1,1'-binaphthyl, 2,2'-bis[bis(4-dimethylamino-3,5-diethylphenyl)

phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl, 2,2'-bis[bis[4-(pyrrolidin-1-yl)phenyl]phosphino]-1,1'-binaphthyl or the like, particularly preferably 2,2'-bis[bis(4-dimethylamino-3,5-dimethylphenyl)phosphino]-1,1'-binaphthyl.

As compound (II), one wherein $R^4$ is a hydrogen atom or an unsubstituted $C_{1-6}$ alkyl group, and $R^5$ and $R^6$ are each an unsubstituted $C_{1-6}$ alkyl group is preferable. In addition, one wherein $R^4$ is a hydrogen atom, and

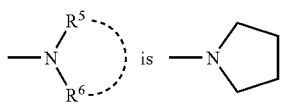

is also preferable.

Preferably, compound (II) is specifically 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl, 2,2'-bis[bis[4-(pyrrolidin-1-yl)phenyl]phosphino]-1,1'-binaphthyl or the like, more preferably 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl or 2,2'-bis[bis(4-dimethylamino-3,5-diisopropylphenyl)phosphino]-1,1'-binaphthyl, particularly preferably 2,2'-bis[bis(4-dimethylamino-3,5-dimethylphenyl)phosphino]-1,1'-binaphthyl.

A production method of compound (I) and compound (II) is shown in the following. Since compound (I) is encompassed in compound (II), only a production method of compound (II) is shown in the following.

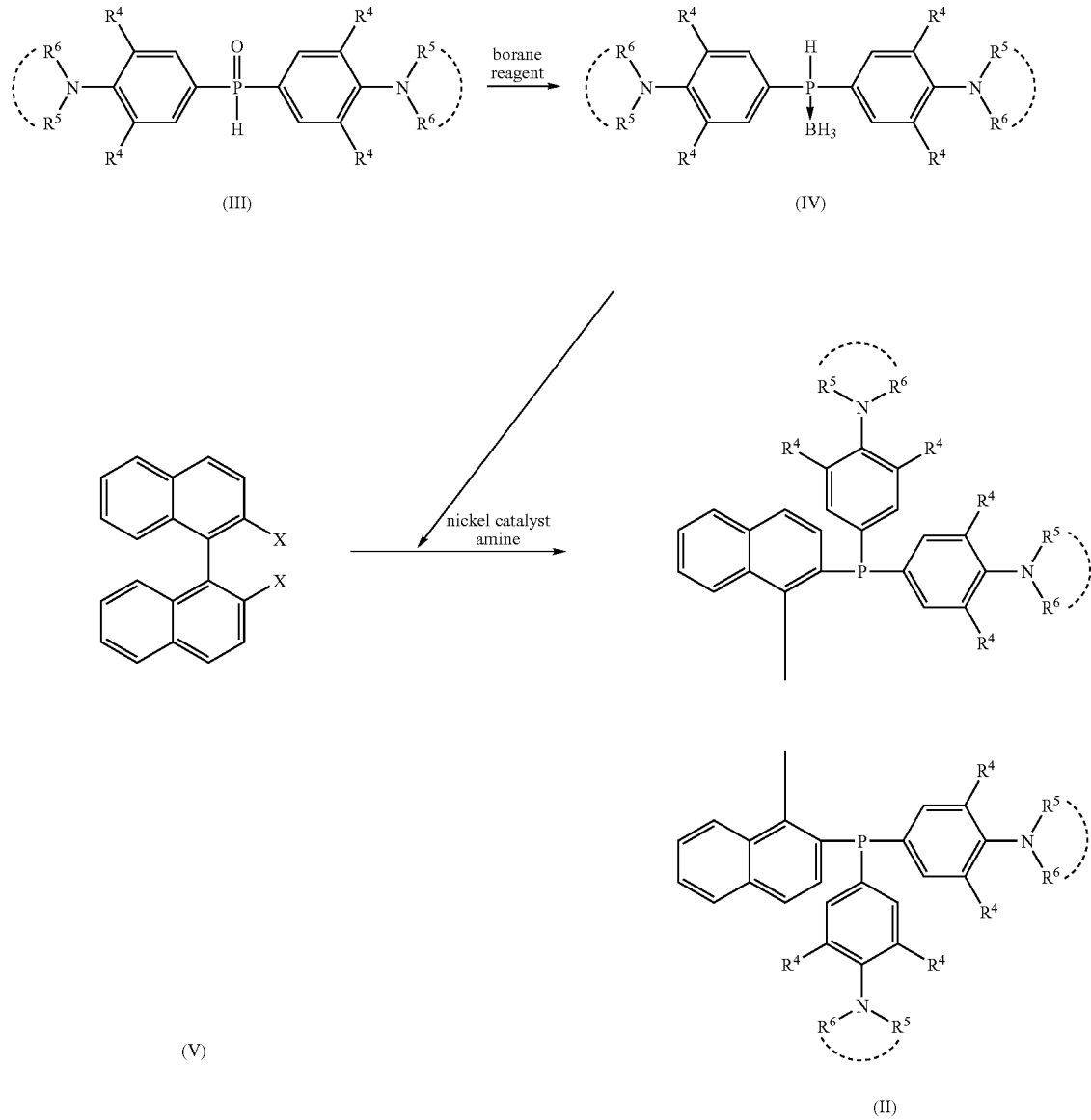

wherein X is a leaving group such as bromine, iodine, trifluoromethanesulfonyloxy, methanesulfonyloxy and the like, and other symbols are as defined above.

Compound (III) can be produced according to the method described in the Journal of Organic Chemistry, vol. 33, page 3690, 1968.

In addition, compound (IV) can be produced by the method described in WO2004/101580, namely, by converting compound (III) in a solvent in the presence of a borane reagent. Of compounds (IV), a compound represented by the formula

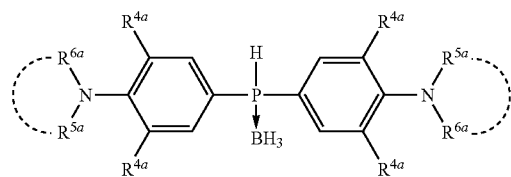

wherein $R^{4a}$ is a hydrogen atom or a $C_{1-6}$ alkyl group optionally having substituent(s), and $R^{5a}$ and $R^{6a}$ are each a $C_{1-6}$ alkyl group optionally having substituent(s), or the formula

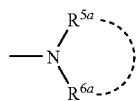

is a group represented by the formula

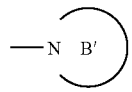

wherein ring B' is a 3- to 8-membered ring optionally having substituent(s), provided that bis(4-dimethylaminophenyl)phosphine-borane complex is excluded, or a salt thereof, is a novel compound.

As the "$C_{1-6}$ alkyl group optionally having substituent(s)" for $R^{4a}$, $R^{5a}$ or $R^{6a}$, those similar to the aforementioned "$C_{1-6}$ alkyl group optionally having substituent(s)" for $R^4$, $R^5$ or $R^6$ can be mentioned. $R^{4a}$, $R^{5a}$ and $R^{6a}$ are each preferably a $C_{1-6}$ alkyl group optionally having substituent(s). In addition, as the "3- to 8-membered ring optionally having substituent(s)" for ring B', those similar to the aforementioned "3- to 8-membered ring optionally having substituent(s)" for ring B can be mentioned.

Compound (V) can be produced according to a method known per se, for example, the method described in Tetrahedron Letters, vol. 31, page 985, 1990, the Journal of Organic Chemistry, vol. 58, page 1945, 1993, and the like. The compound (V) thus obtained may be used as a reaction mixture without isolation for a reaction with compound (IV).

Compound (II) can be produced by the method described in WO2003/048174, namely, by reacting compound (IV) with compound (V) in a solvent in the presence of an amine and a nickel catalyst.

The resulting product can be isolated from the reaction mixture according to a conventional method, and easily purified by a separation method such as recrystallization, distillation, chromatography and the like.

As a salt of compound (I) or compound (IV), for example, a salt with an inorganic acid (e.g., hydrochloric acid, hydrobromic acid, nitric acid, sulfuric acid, phosphoric acid and the like), a salt with an organic acid (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like) and the like can be used. In addition, when compound (I) or compound (IV) has an acidic group such as carboxyl group and the like, a salt with an inorganic base (e.g., alkali metal or alkaline earth metal such as sodium, potassium, calcium, magnesium and the like, ammonia and the like), a salt with an organic base (e.g., trimethylamine, triethylamine, pyridine, picoline, ethanolamine, diethanolamine, triethanolamine, dicyclohexylamine, N,N'-dibenzylethylenediamine and the like) and the like can be used.

Examples of the "transition metal" in the transition metal complex of the present invention include rhodium, ruthenium, iridium, palladium, nickel, cobalt, platinum, iron, gold, silver, copper and the like. Of these, rhodium, ruthenium, iridium, palladium, nickel and copper are preferable, and rhodium, ruthenium and palladium are particularly preferable.

The transition metal complex of the present invention can be produced according to a known method.

When a rhodium complex is to be produced, for example, it can be produced by reacting compound (II) with di-μ-chlorobis[($\eta^2,\eta^2$-1,5-cyclooctadiene)rhodium (I)] in a solvent according to the method described in Journal of the American Chemical Society, vol. 94, page 6429, 1972. It can also be produced by reacting compound (II) with di-μ-chlorobis[($\eta^2,\eta^2$-1,5-cyclooctadiene)rhodium (I)] and silver perchlorate according to the method described in Organic Syntheses, vol. 67, page 33, 1989.

When a ruthenium complex is to be produced, for example, it can be produced by heating compound (II) and di-μ-chlorobis[($\eta^6$-benzene)chlororuthenium (II)] with stirring in N,N-dimethylformamide (DMF), and stirring the obtained product in the presence of sodium acetate in methanol according to the method described in the Journal of Organic Chemistry, vol. 57, page 4053, 1992. In addition, it can also be produced by heating compound (II) and ($\eta^2,\eta^2$-1,5-cyclooctadiene)bis($\eta^3$-2-methylallyl)ruthenium (II) in hexane/toluene with stirring according to the method described in Tetrahedron Asymmetry, vol. 2, page 43, 1991. It can also be produced by heating compound (II) and di-μ-chlorobis[($\eta^6$-benzene)chlororuthenium (II)] with stirring in ethanol/benzene according to the method described in the Journal of Organic Chemistry, vol. 59, page 3064, 1994. Moreover, it can be produced by stirring a ruthenium complex obtained by the above-mentioned method, which comprises compound (II), and diamine in N,N-dimethylformamide (DMF) according to the method described in Angewandte Chemie International Edition, vol. 37, page 1703, 1998.

When an iridium complex is to be produced, for example, it can be produced by reacting compound (II) with [Ir(cod)(CH$_3$CN)$_2$]BF$_4$ in a solvent according to the method described in Journal of Organometallic Chemistry, vol. 428, page 213, 1992.

When a palladium complex is to be produced, for example, it can be produced by reacting compound (II) with ($\eta^3$-allyl)($\eta^5$-cyclopentadienyl)palladium (II) according to the method described in Organometallics, vol. 12, page 4188, 1993. In addition, it can be produced by reacting compound (II) with dichlorobis(acetonitrile)palladium (II). A palladium complex tetrafluoroborate can be produced by further stirring the obtained palladium complex with silver tetrafluoroborate in aqueous dichloromethane according to the method described in Journal of the American Chemical Society, vol. 121, page 5450, 1999.

When a nickel complex is to be produced, for example, it can be produced by heating compound (II) with anhydrous nickel bromide with stirring in the presence of a solvent according to the method described in "5$^{th}$ edition Jikken Kagaku Kouza" vol. 21, organic transition metal compound, supermolecular complex, pages 293-294 (2004), edited by Chemical Society of Japan (Maruzen).

When a copper complex is to be produced, for example, it can be produced by reacting compound (II) with copper(I) chloride according to the method described in "5$^{th}$ edition Jikken Kagaku Kouza" vol. 21, organic transition metal compound, supermolecular complex, page 357 (2004), edited by Chemical Society of Japan (Maruzen). In addition, it can be produced by stirring compound (II) and tetrakis(acetonitrile)copper(I) perchlorate in dichloromethane according to the method described in the Journal of Organic Chemistry, vol. 63, page 6090, 1998.

Specific examples of the rhodium complex include the following (in the following formulae of transition metal complexes, L is compound (II) of the present invention, Ar is benzene optionally having substituent(s), Cp* is pentamethylcyclopentadienyl, Cp is cyclopentadienyl, cod is 1,5-cyclooctadiene, Tf is trifluoromethanesulfonyl, nbd is norbornadiene, Ph is phenyl, Ac is acetyl, Et is ethyl, dmf is N,N-dimethylformamide, 2-methylallyl is $\eta^3$-2-methylallyl, en is ethylenediamine, dpen is 1,2-diphenylethylenediamine, daipen is 1,1-di(4-anisyl)-2-isopropyl-1,2-ethylenediamine, and n is an integer of not less than 1).

While 1,2-diphenylethylenediamine and 1,1-di(4-anisyl)-2-isopropyl-1,2-ethylenediamine include an (R) form, an (S) form and a mixture of an (R) form and an (S) form (no limitation on the ratio thereof), an optically active form is preferable.

[RhCl(L)]$_2$, [RhBr(L)]$_2$, [RhI(L)]$_2$, [RhCp*(L)]$_2$, [Rh(cod)(L)]OTf, [Rh(cod)(L)]BF$_4$, [Rh(cod)(L)]ClO$_4$, [Rh(cod)(L)]PF$_6$, [Rh(cod)(L)]BPh$_4$, [Rh(nbd)(L)]OTf, [Rh(nbd)(L)]BF$_4$, [Rh(nbd)(L)]ClO$_4$, [Rh(nbd)(L)]PF$_6$, [Rh(nbd)(L)]BPh$_4$, [Rh(L)(CH$_3$OH)$_2$]OTf, [Rh(L)(CH$_3$OH)$_2$]BF$_4$, [Rh(L)(CH$_3$OH)$_2$]ClO$_4$, [Rh(L)(CH$_3$OH)$_2$]PF$_6$, [Rh(L)(CH$_3$OH)$_2$]BPh$_4$ Specific examples of the ruthenium complex include the following.

[RuCl$_2$(L)]$_n$, [RuBr$_2$(L)]$_n$, [RuI$_2$(L)]$_n$, [Ru(OAc)$_2$(L)], [Ru(O$_2$CCF$_3$)$_2$(L)], (NH$_2$Me$_2$)[{RuCl(L)}$_2$($\mu$-Cl)$_3$], (NH$_2$Et$_2$)[{RuCl(L)}$_2$($\mu$-Cl)$_3$], (NH$_2$Me$_2$)[{RuBr(L)}$_2$($\mu$-Br)$_3$], (NH$_2$Et$_2$)[{RuBr(L)}$_2$($\mu$-Br)$_3$], (NH$_2$Me$_2$)[{RuI(L)}$_2$($\mu$-I)$_3$], (NH$_2$Et$_2$) [{RuI(L)}$_2$($\mu$-I)$_3$], [Ru$_2$Cl$_4$(L)$_2$(NEt$_3$)], [RuCl$_2$(L)(dmf)$_n$], [Ru(2-methylallyl)$_2$(L)], [RuCl(Ar)(L)]Cl, [RuCl(Ar)(L)]Br, [RuCl(Ar)(L)]I, [RuCl(Ar)(L)]OTf, [RuCl(Ar)(L)]ClO$_4$, [RuCl(Ar)(L)]PF$_6$, [RuCl(Ar)(L)]BF$_4$, [RuCl(Ar)(L)]BPh$_4$, [RuBr(Ar)(L)]Cl, [RuBr(Ar)(L)]Br, [RuBr(Ar)(L)]I, [RuI(Ar)(L)]Cl, [RuI(Ar)(L)]Br, [RuI(Ar)(L)]I, [Ru(L)](OTf)$_2$, [Ru(L)](BF$_4$)$_2$, [Ru(L)](ClO$_4$)$_2$, [Ru(L)](PF$_6$)$_2$, [Ru(L)](BPh$_4$)$_2$, [RuH(L)$_2$]Cl, [RuH(L)$_2$]OTf, [RuH(L)$_2$]BF$_4$, [RuH(L)$_2$]ClO$_4$, [RuH(L)$_2$]PF$_6$, [RuH(L)$_2$]BPh$_4$, [RuH(CH$_3$CN)(L)]Cl, [RuH(CH$_3$CN)(L)]OTf, [RuH(CH$_3$CN)(L)]BF$_4$, [RuH(CH$_3$CN)(L)]ClO$_4$, [RuH(CH$_3$CN)(L)]PF$_6$, [RuH(CH$_3$CN)(L)]BPh$_4$, [RuCl(L)]OTf, [RuCl(L)]BF$_4$, [RuCl (L)]ClO$_4$, [RuCl(L)]PF$_6$, [RuCl(L)]BPh$_4$, [RuBr(L)]OTf, [RuBr(L)]BF$_4$, [RuBr(L)]ClO$_4$, [RuBr(L)]PF$_6$, [RuBr(L)]BPh$_4$, [RuI(L)]OTf, [RuI(L)]BF$_4$, [RuI(L)]ClO$_4$, [RuI(L)]PF$_6$, [RuI(L)]BPh$_4$, [RUCl$_2$(L)(en)], [RuCl$_2$(L)(dpen)], [RuCl$_2$(L)(daipen)], [RuH($\eta^1$-BH$_4$)(L)(en)], [RuH($\eta^1$-BH$_4$)(L)(daipen)], [RuH($\eta^1$-BH$_4$)(L)(dpen)]

As the diamine ligand corresponding to en, dpen and daipen, which are diamine ligands in the aforementioned [RuCl$_2$(L)(en)], [RuCl$_2$(L)(dpen)] and [RuCl$_2$(L)(daipen)], for examples, 1,2-cyclohexanediamine, 1,2-cycloheptanediamine, 2,3-dimethylbutanediamine, 1-methyl-2,2-diphenyl-1,2-ethylenediamine, 1-isobutyl-2,2-diphenyl-1,2-ethylenediamine, 1-isopropyl-2,2-diphenyl-1,2-ethylenediamine, 1,1-di(4-anisyl)-2-methyl-1,2-ethylenediamine, 1,1-di(4-anisyl)-2-isobutyl-1,2-ethylenediamine, 1,1-di(4-anisyl)-2-benzyl-1,2-ethylenediamine, 1-methyl-2,2-dinaphthyl-1,2-ethylenediamine, 1-isobutyl-2,2-dinaphthyl-1,2-ethylenediamine, 1-isopropyl-2,2-dinaphthyl-1,2-ethylenediamine, propanediamine, butanediamine, phenylenediamine and the like can be used.

Specific examples of the iridium complex include the following.

[IrCl(L)]$_2$, [IrBr(L)]$_2$, [IrI(L)]$_2$, [IrCp(L)]$_2$, [Ir(cod)(L)]OTf, [Ir(cod)(L)]BF$_4$, [Ir(cod)(L)]ClO$_4$, [Ir(cod)(L)]PF$_6$, [Ir(cod)(L)]BPh$_4$, [Ir(nbd)(L)]OTf, [Ir(nbd)(L)]BF$_4$, [Ir(nbd)(L)]ClO$_4$, [Ir(nbd)(L)]PF$_6$, [Ir(nbd)(L)]BPh$_4$ Specific examples of the palladium complex include the following.

[PdCl$_2$(L)], [PdBr$_2$(L)], [PdI$_2$(L)], [Pd($\pi$-allyl)(L)]Cl, [Pd($\pi$-allyl)(L)]OTf, [Pd($\pi$-allyl)(L)]BF$_4$, [Pd($\pi$-allyl)(L)]ClO$_4$, [Pd($\pi$-allyl)(L)]PF$_6$, [Pd($\pi$-allyl)(L)]BPh$_4$, [Pd(L)](OTf)$_2$, [Pd(L)](BF$_4$)$_2$, [Pd(L)](ClO$_4$)$_2$, [Pd(L)](PF$_6$)$_2$, [Pd(L)](BPh$_4$)$_2$, [Pd(L)$_2$], [Pd(L)(H$_2$O)$_2$](OTf)$_2$, [Pd(L)(H$_2$O)$_2$](BF$_4$)$_2$, [Pd(L)(H$_2$O)$_2$](ClO$_4$)$_2$, [Pd(L)(H$_2$O)$_2$](PF$_6$)$_2$, [Pd(L)(H$_2$O)$_2$](BPh$_4$)$_2$, [{Pd(L)}$_2$($\mu$-OH)$_2$](OTf)$_2$, [{Pd(L)}$_2$($\mu$-OH)$_2$](BF$_4$)$_2$, [{Pd(L)}$_2$($\mu$-OH)$_2$](ClO$_4$)$_2$, [{Pd(L)}$_2$($\mu$-OH)$_2$](PF$_6$)$_2$, [{Pd(L)}$_2$($\mu$-OH)$_2$](BPh$_4$)$_2$ Specific examples of the nickel complex include the following.

[NiCl$_2$(L)], [NiBr$_2$(L)], [NiI$_2$(L)], [Ni($\pi$-allyl)(L)]Cl, [Ni(cod)(L)], [Ni(nbd)(L)]

Specific examples of the copper complex include the following.

[CuCl(L)], [CuBr(L)], [CuI(L)], [CuH(L)], [Cu($\eta^1$-BH$_4$)(L)], [Cu(Cp)(L)], [Cu(Cp*)(L)], [Cu(L)(CH$_3$CN)$_2$]OTf, [Cu(L)(CH$_3$CN)$_2$]BF$_4$, [Cu(L)(CH$_3$CN)$_2$]ClO$_4$, [Cu(L)(CH$_3$CN)$_2$]PF$_6$, [Cu(L)(CH$_3$CN)$_2$]BPh$_4$ Of the transition metal complexes of the present invention, particularly preferred are (1) [Ru(OAc)$_2$(L)];
(2) [RuCl$_2$(L)(dmf)$_n$];
(3) [RuCl(Ar)(L)]Cl;
(4) [Ru(2-methylallyl)$_2$(L)];
(5) [RuCl$_2$(L)(X)];
(6) (NH$_2$Et$_2$)[{RuCl(L)}$_2$($\mu$-Cl)$_3$];
(7) [Rh(Y)(L)]Z;
(8) [PdCl$_2$(L)]; and
(9) [{Pd(L)}$_2$($\mu$-OH)$_2$]Z$_2$ wherein L is 2,2'-bis[bis(4-dimethylaminophenyl)phosphino]-1,1'-binaphthyl, 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, 2,2'-bis[bis(4-diethylaminophenyl)phosphino]-1,1'-binaphthyl or 2,2'-bis[bis[4-(pyrrolidin-1-yl)phenyl]phosphino]-1,1'-binaphthyl, Ac is acetyl, dmf is N,N-dimethylformamide, n is an integer of not less than 1, Ar is benzene optionally having substituent(s), 2-methylallyl is $\eta^3$-2-methylallyl, X is ethylenediamine, 1,2-diphenylethylenediamine or 1,1-di(4-anisyl)-2-isopropyl-1,2-ethylenediamine, Y is 1,5-cyclooctadiene or norbornadiene, Z is a counter anion and trifluoromethanesulfonate, tetrafluoroborate, perchlorate, hexafluorophosphate or tetraphenylborate, and the like.

As the substituent of "benzene optionally having substituent(s)" for the above-mentioned Ar, for example, a $C_{1-6}$ alkyl group such as methyl, ethyl, isopropyl, butyl, isobutyl, sec-butyl, tert-butyl and the like can be mentioned. One to three selected from these substituents may present at substitutable position(s). As Ar, benzene is preferable.

When the thus-obtained transition metal complex of the present invention is used as a catalyst, it may be used after increasing the purity of the complex, or used without purifying the complex.

In addition, when the transition metal complex of the present invention is used as a catalyst, the "transition metal complex" may be prepared in the reaction system of the asymmetric synthesis reaction, or a transition metal complex prepared and isolated in advance may be used.

Using the transition metal complex of the present invention for an asymmetric synthesis reaction such as asymmetric reduction reaction and the like, a compound having the objective steric structure can be produced. The reaction examples are shown below.

1. Asymmetric Reduction of Ketone (1)

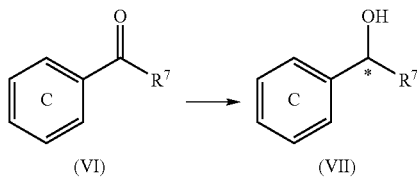

wherein ring C is a benzene ring optionally having substituent(s), $R^7$ is a $C_{1-6}$ alkyl group optionally having substituent(s), and * shows the position of an asymmetric carbon.

Optically active compound (VII) can be obtained by subjecting compound (VI) to a reduction reaction in the presence of the transition metal complex of the present invention.

Examples of the substituent of ring C include nitro, nitroso, cyano, hydroxy, optionally halogenated $C_{1-6}$ alkyl group (e.g., methyl, trichloromethyl, trifluoromethyl, ethyl, propyl, isopropyl, butyl, isobutyl, sec-butyl, tert-butyl, pentyl, hexyl and the like), $C_{1-6}$ alkoxy group (e.g., methoxy, ethoxy, propoxy, isopropoxy, butoxy, isobutoxy, sec-butoxy, tert-butoxy, pentoxy, hexyloxy and the like), formyl, $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like), carboxyl, N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), N,N-di-$C_{1-6}$ alkylcarbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl and the like) and the like can be mentioned. One to three selected from these substituents may be present at substitutable position(s).

In addition, the substituents of ring C may be bonded to each other to form a benzene ring.

As the "$C_{1-6}$ alkyl group" of the "$C_{1-6}$ alkyl group optionally having substituent(s)" for $R^7$, methyl, ethyl, propyl, isopropyl, butyl, isobutyl, sec-butyl, tert-butyl, pentyl, hexyl and the like can be mentioned.

As the "substituent" of the "$C_{1-6}$ alkyl group optionally having substituent(s)" for $R^7$, nitro, nitroso, cyano, hydroxy, $C_{1-6}$ alkoxy group (e.g., methoxy, ethoxy, propoxy, isopropoxy, butoxy, isobutoxy, sec-butoxy, tert-butoxy, pentoxy, hexyloxy and the like), formyl, $C_{1-6}$ alkyl-carbonyl group (e.g., acetyl, propionyl, butyryl, isobutyryl, valeryl, isovaleryl, pivaloyl and the like), $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like), carboxyl, N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), N,N-di-$C_{1-6}$ alkylcarbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl and the like) and the like can be mentioned. One to three selected from these substituents may be present at substitutable position(s).

In the asymmetric reduction reaction of compound (VI), the amount of the transition metal complex of the present invention to be used is about 0.01 mmol to about 1 mol, preferably about 1 mmol to about 10 mmol, relative to 1 mol of compound (VI).

In the asymmetric reduction reaction of compound (VI), a hydrogen gas is used as a hydrogen source. The hydrogen pressure in the reaction is about 0.1 MPa to 10 MPa, preferably about 0.1 MPa to 5 MPa.

The asymmetric reduction reaction of compound (VI) is carried out in a solvent. As the solvent to be used, a solvent selected from alcohol solvents (e.g., methanol, ethanol, n-propanol, isopropanol etc.), hydrocarbon solvents (e.g., hexane, benzene, toluene, xylene etc.), ether solvents (e.g., diethyl ether, diisopropyl ether, tert-butyl methyl ether, dioxane, tetrahydrofuran etc.), ester solvents (e.g., ethyl acetate, isopropyl acetate), ketone solvents (e.g., acetone, methyl ethyl ketone etc.), nitrile solvents (e.g., acetonitrile, propionitrile etc.), sulfoxide solvents (e.g., dimethyl sulfoxide etc.) and amide solvents (e.g., N,N-dimethylformamide etc.), or a mixed solvent of two or more kinds thereof can be mentioned. Of these, alcohol solvents (e.g., methanol, ethanol, n-propanol, isopropanol etc.), particularly isopropanol, are preferable.

The reaction temperature of the asymmetric reduction reaction of compound (VI) is preferably about 0° C. to about 180° C., particularly about 20° C. to about 100° C.

The asymmetric reduction reaction of compound (VI) is desirably carried out by the addition of a base. As the "base", an inorganic base is preferable. Of these, potassium hydroxide, potassium isopropoxide, potassium tert-butoxide and the like are more preferable, and potassium tert-butoxide is particularly preferable. The amount of the "base" to be used is about 0.001 mmol to about 10 mol, preferably about 1 mmol to about 100 mmol, relative to 1 mol of compound (VI).

In addition, the asymmetric reduction reaction of compound (VI) can also be carried out under the same conditions using a generally-used transition metal complex other than the transition metal complex of the present invention. Examples of the transition metal complex other than that of the present invention include a transition metal complex, wherein a transition metal is rhodium, ruthenium, nickel or cobalt.

2. Asymmetric Reduction of Olefin (1)

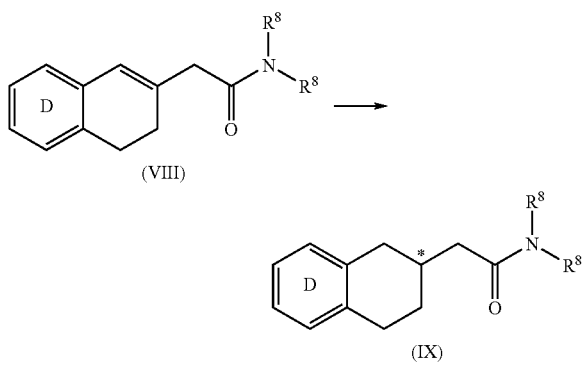

wherein ring D is a benzene ring optionally having substituent(s), $R^8$ is a $C_{1-6}$ alkyl group optionally having substituent(s), and * shows the position of an asymmetric carbon.

An optically active compound (IX) useful as a synthetic intermediate for a pharmaceutical agent can be obtained by subjecting compound (VIII) to a reduction reaction (hydrogenation reaction) in the presence of the transition metal complex of the present invention.

As the substituent of ring D, nitro, nitroso, cyano, hydroxy, optionally halogenated $C_{1-6}$ alkyl group (e.g., methyl, trichloromethyl, trifluoromethyl, ethyl, propyl, isopropyl, butyl, isobutyl, sec-butyl, tert-butyl, pentyl, hexyl and the like), $C_{1-6}$ alkoxy group (e.g., methoxy, ethoxy, propoxy, isopropoxy, butoxy, isobutoxy, sec-butoxy, tert-butoxy, pentoxy, hexyloxy and the like), formyl, $C_{1-6}$ alkyl-carbonyl group (e.g., acetyl, propionyl, butyryl, isobutyryl, valeryl, isovaleryl, pivaloyl and the like), $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like), carboxyl, N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), N,N-di-$C_{1-6}$ alkylcarbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl and the like) and the like can be mentioned. One to three selected from these substituents may be present at substitutable position(s).

As the "$C_{1-6}$ alkyl group" of the "$C_{1-6}$ alkyl group optionally having substituent(s)" for $R^8$, methyl, ethyl, propyl, isopropyl, butyl, isobutyl, sec-butyl, tert-butyl, pentyl, hexyl and the like can be mentioned.

As the "substituent" of the "$C_{1-6}$ alkyl group optionally having substituent(s)" for $R^8$, nitro, nitroso, cyano, hydroxy, $C_{1-6}$ alkoxy group (e.g., methoxy, ethoxy, propoxy, isopropoxy, butoxy, isobutoxy, sec-butoxy, tert-butoxy, pentoxy, hexyloxy and the like), formyl, $C_{1-6}$ alkyl-carbonyl group (e.g., acetyl, propionyl, butyryl, isobutyryl, valeryl, isovaleryl, pivaloyl and the like), $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentoxycarbonyl, hexyloxycarbonyl and the like), carboxyl, N-mono-$C_{1-6}$ alkyl-carbamoyl group (e.g., N-methylcarbamoyl, N-ethylcarbamoyl, N-propylcarbamoyl, N-isopropylcarbamoyl, N-butylcarbamoyl, N-isobutylcarbamoyl, N-tert-butylcarbamoyl and the like), N,N-di-$C_{1-6}$ alkylcarbamoyl group (e.g., N,N-dimethylcarbamoyl, N,N-diethylcarbamoyl, N,N-dipropylcarbamoyl, N,N-diisopropylcarbamoyl, N-ethyl-N-methylcarbamoyl and the like) and the like can be mentioned. One to three selected from these substituents may be present at substitutable position(s).

As the salts of compound (VIII) and compound (IX), those similar to the aforementioned salts of compound (I) and compound (IV) are used.

In the asymmetric reduction reaction of compound (VIII), the amount of the transition metal complex of the present invention to be used is about 0.01 mmol to about 1 mol, preferably about 1 mmol to about 10 mmol, relative to 1 mol of compound (VIII).

In the asymmetric reduction reaction of compound (VIII), a hydrogen gas is used as a hydrogen source. The hydrogen pressure during the reaction is about 0.1 MPa to 10 MPa, preferably about 0.1 MPa to 5 MPa.

The asymmetric reduction reaction of compound (VIII) is performed in a solvent. The solvent to be used includes a solvent selected from alcohol solvents (e.g., methanol, ethanol, n-propanol, isopropanol etc.), hydrocarbon solvents (e.g., hexane, benzene, toluene, xylene etc.), ether solvents (e.g., diethyl ether, diisopropyl ether, tert-butyl methyl ether, dioxane, tetrahydrofuran etc.), ester solvents (e.g., ethyl acetate, isopropyl acetate), ketone solvents (e.g., acetone, methyl ethyl ketone etc.), nitrile solvents (e.g., acetonitrile, propionitrile etc.), sulfoxide solvents (e.g., dimethyl sulfoxide etc.) and amide solvents (e.g., N,N-dimethylformamide etc.) or a mixed solvent of two or more kinds thereof. Of these, alcohol solvents (e.g., methanol, ethanol, n-propanol, isopropanol etc.), particularly ethanol, are preferable.

The reaction temperature of the asymmetric reduction reaction of compound (VIII) is preferably about 0° C. to about 180° C., particularly about 20° C. to about 100° C.

In addition, the asymmetric reduction reaction of compound (VIII) can also be carried out under the same conditions using a generally-used transition metal complex other than the transition metal complex of the present invention. Examples of the transition metal complex other than that of the present invention include a transition metal complex, wherein a transition metal is rhodium, ruthenium, nickel or cobalt.

3. Asymmetric Reduction of Ketone (2)

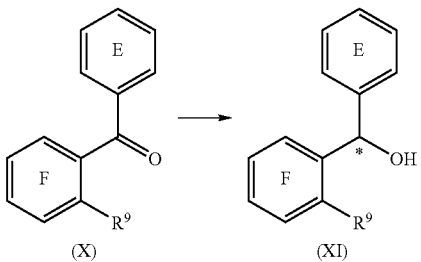

wherein ring E and ring F are each a benzene ring optionally having substituent(s), $R^9$ is an amino group optionally having substituent(s), and * shows the position of an asymmetric carbon.

An optically active compound (XI) can be obtained by subjecting compound (X) to a reduction reaction in the presence of the transition metal complex of the present invention.

As the substituent that ring E and ring F may have, a halogen atom (fluorine atom, chlorine atom, bromine atom, iodine atom), a hydroxy group, a $C_{1-6}$ alkyl group optionally substituted with one or more halogen atoms (fluorine atom, chlorine atom, bromine atom, iodine atom) (methyl, trichloromethyl, trifluoromethyl, ethyl, propyl, isopropyl, butyl, isobutyl, sec-butyl, tert-butyl, pentyl, hexyl and the like), a $C_{1-6}$ alkoxy group optionally substituted with one or more halogen atoms (fluorine atom, chlorine atom, bromine atom, iodine atom) (methoxy, trichloromethoxy, trifluoromethoxy, ethoxy, propoxy, isopropoxy, butoxy, isobutoxy, sec-butoxy, tert-butoxy, pentoxy, hexyloxy and the like) and the like can be mentioned. Of these, a halogen atom (fluorine atom, chlorine atom, bromine atom, iodine atom) and a $C_{1-6}$ alkoxy group (methoxy, ethoxy, propoxy, isopropoxy, butoxy, isobutoxy, sec-butoxy, tert-butoxy, pentoxy, hexyloxy and the like) and the like are preferable.

As the "substituent" of the "amino group optionally having substituent(s)" for $R^9$, a $C_{1-6}$ alkyl group (methyl, ethyl, propyl, isopropyl, butyl, isobutyl, sec-butyl, tert-butyl, pentyl, hexyl and the like), a halogen atom (fluorine atom, chlorine atom, bromine atom, iodine atom), a $C_{1-6}$ acyl group (formyl, acetyl, propionyl, butyryl and the like), a protecting group (benzyloxycarbonyl, methoxycarbonyl, ethoxycarbonyl, propoxycarbonyl, isopropoxycarbonyl, butoxycarbonyl, isobutoxycarbonyl, tert-butoxycarbonyl and the like) can be mentioned. The number of the substituents is 1 or 2.

In the asymmetric reduction reaction of compound (X), the amount of the transition metal complex of the present invention to be used is about 0.01 mmol to about 1 mol, preferably about 1 mmol to about 10 mmol, relative to 1 mol of compound (X).

In the asymmetric reduction reaction of compound (X), a hydrogen gas is used as a hydrogen source. The hydrogen pressure during the reaction is about 0.1 MPa to 10 MPa, preferably about 0.1 MPa to 5 MPa.

The asymmetric reduction reaction of compound (X) is performed in a solvent. As the solvent to be used, a solvent selected from alcohol solvents (e.g., methanol, ethanol, n-propanol, isopropanol etc.), hydrocarbon solvents (e.g., hexane, benzene, toluene, xylene etc.), ether solvents (e.g., diethyl ether, diisopropyl ether, tert-butyl methyl ether, dioxane, tetrahydrofuran etc.), ester solvents (e.g., ethyl acetate, isopropyl acetate), ketone solvents (e.g., acetone, methyl ethyl ketone etc.), nitrile solvents (e.g., acetonitrile, propionitrile etc.), sulfoxide solvents (e.g., dimethyl sulfoxide etc.) and amide solvents (e.g., N,N-dimethylformamide etc.) or a mixed solvent of two or more kinds thereof can be mentioned. Of these, alcohol solvents (e.g., methanol, ethanol, n-propanol, isopropanol etc.), particularly isopropanol, are preferable.

The reaction temperature in the asymmetric reduction reaction of compound (X) is preferably about 0° C. to about 180° C., particularly about 20° C. to about 100° C.

The asymmetric reduction reaction of compound (X) is desirably performed by the addition of a base. As the "base", an inorganic base is preferable. Of these, potassium hydroxide, potassium isopropoxide, potassium tert-butoxide and the like are more preferable, and potassium tert-butoxide is particularly preferable. The amount of the "base" to be used is about 0.001 mmol to about 10 mol, preferably about 1 mmol to about 100 mmol, relative to 1 mol of compound (X).

In addition, the asymmetric reduction reaction of compound (X) can also be carried out under the same conditions using a generally-used transition metal complex other than the transition metal complex of the present invention. Examples of the transition metal complex other than that of the present invention include a transition metal complex, wherein a transition metal is rhodium, ruthenium, nickel or cobalt.

4. Asymmetric Reduction of Olefin (2)

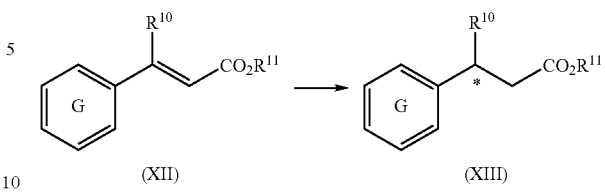

wherein ring G is a benzene ring optionally further having substituent(s), $R^{10}$ is an amino group optionally having substituent(s), $R^{11}$ is a hydrogen atom or a $C_{1-6}$ alkyl group optionally having substituent(s), and * shows the position of an asymmetric carbon.

An optically active compound (XIII) can be obtained by subjecting compound (XII) to a reduction reaction in the presence of the transition metal complex of the present invention.

As the "amino group optionally having substituent(s)" for $R^{10}$, those similar to the above-mentioned "amino group optionally having substituent(s)" for $R^9$ can be mentioned.

As the "$C_{1-6}$ alkyl group optionally having substituent(s)" for $R^{11}$, those similar to the above-mentioned "$C_{1-6}$ alkyl group optionally having substituent(s)" for $R^8$ can be mentioned.

In the asymmetric reduction reaction of compound (XII), the amount of the transition metal complex of the present invention to be used is about 0.01 mmol to about 1 mol, preferably about 1 mmol to about 10 mmol, relative to 1 mol of compound (XII).

In the asymmetric reduction reaction of compound (XII), a hydrogen gas is used as a hydrogen source. The hydrogen pressure during the reaction is about 0.1 MPa to 10 MPa, preferably about 0.1 MPa to 5 MPa.

The asymmetric reduction reaction of compound (XII) is performed in a solvent. As the solvent to be used, a solvent selected from alcohol solvents (e.g., methanol, ethanol, n-propanol, isopropanol etc.), hydrocarbon solvents (e.g., hexane, benzene, toluene, xylene etc.), ether solvents (e.g., diethyl ether, diisopropyl ether, tert-butyl methyl ether, dioxane, tetrahydrofuran etc.), ester solvents (e.g., ethyl acetate, isopropyl acetate), ketone solvents (e.g., acetone, methyl ethyl ketone etc.), nitrile solvents (e.g., acetonitrile, propionitrile etc.), sulfoxide solvents (e.g., dimethyl sulfoxide etc.) and amide solvents (e.g., N,N-dimethylformamide etc.), or a mixed solvent of two or more kinds thereof can be mentioned. Of these, alcohol solvents (e.g., methanol, ethanol, n-propanol, isopropanol etc.), particularly ethanol, are preferable.

The reaction temperature of the asymmetric reduction reaction of compound (XII) is preferably about 0° C. to about 180° C., particularly preferably about 20° C. to about 100° C.

In addition, the asymmetric reduction reaction of compound (XII) can also be carried out under the same conditions using a generally-used transition metal complex other than the transition metal complex of the present invention. Examples of the transition metal complex other than that of the present invention include a transition metal complex, wherein a transition metal is rhodium, ruthenium, nickel or cobalt.

5. Asymmetric Reduction of Olefin (3)

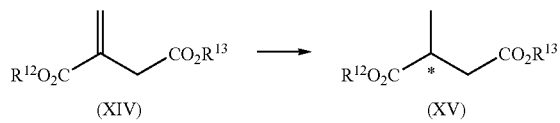

wherein $R^{12}$ and $R^{13}$ are the same or different and each is a hydrogen atom or a $C_{1-6}$ alkyl group optionally having substituent(s), and * shows the position of an asymmetric carbon.

An optically active compound (XV) can be obtained by subjecting compound (XIV) to a reduction reaction in the presence of the transition metal complex of the present invention.

As the "$C_{1-6}$ alkyl group optionally having substituent(s)" for $R^{12}$ and $R^{13}$, those similar to the above-mentioned "$C_{1-6}$ alkyl group optionally having substituent(s)" for $R^8$ can be mentioned.

In the asymmetric reduction reaction of compound (XIV), the amount of the transition metal complex of the present invention to be used is about 0.01 mmol to about 1 mol, preferably about 1 mmol to about 10 mmol, relative to 1 mol of compound (XIV).

In the asymmetric reduction reaction of compound (XIV), a hydrogen gas is used as a hydrogen source. The hydrogen pressure during the reaction is about 0.1 MPa to 10 MPa, preferably about 0.1 MPa to 5 MPa.

The asymmetric reduction reaction of compound (XIV) is performed in a solvent. As the solvent to be used, a solvent selected from alcohol solvents (e.g., methanol, ethanol, n-propanol, isopropanol etc.), hydrocarbon solvents (e.g., hexane, benzene, toluene, xylene etc.), ether solvents (e.g., diethyl ether, diisopropyl ether, tert-butyl methyl ether, dioxane, tetrahydrofuran etc.), ester solvents (e.g., ethyl acetate, isopropyl acetate), ketone solvents (e.g., acetone, methyl ethyl ketone etc.), nitrile solvents (e.g., acetonitrile, propionitrile etc.), sulfoxide solvents (e.g., dimethyl sulfoxide etc.) and amide solvents (e.g., N,N-dimethylformamide etc.), or a mixed solvent of two or more kinds thereof can be mentioned. Of these, alcohol solvents (e.g., methanol, ethanol, n-propanol, isopropanol etc.), particularly ethanol, are preferable.

The reaction temperature of the asymmetric reduction reaction of compound (XIV) is preferably about 0° C. to about 180° C., particularly preferably about 20° C. to about 100° C.

In addition, the asymmetric reduction reaction of compound (XIV) can also be performed under the same conditions using a generally-used transition metal complex other than the transition metal complex of the present invention. Examples of the transition metal complex other than that of the present invention include a transition metal complex, wherein a transition metal is rhodium, ruthenium, nickel or cobalt.

In addition, the transition metal complex of the present invention can be used, besides the above-mentioned reactions, for an asymmetric fluorination reaction of β-ketoester, an isomerization reaction of olefin and the like, whereby the production of an optically active compound useful as a synthetic intermediate of pharmaceutical agents has been enabled.

EXAMPLES

The present invention is explained in detail in the following by referring to Examples and Reference Examples, which are not to be construed as limitative. In the present specification, the room temperature is 10° C. to 35° C. For the measurement of each property in the Examples, the following instruments were used. $^1$H nuclear magnetic resonance spectrum ($^1$H-NMR): DPX300 (manufactured by Bruker), internal standard substance: tetramethylsilane (TMS), $CD_2Cl_2$. $^{13}$C nuclear magnetic resonance spectrum ($^{13}$C-NMR): DPX300 (manufactured by Bruker), internal standard substance: $CDCl_3$, $CD_2Cl_2$. $^{31}$P nuclear magnetic resonance spectrum ($^{31}$P-NMR): DPX300 (manufactured by Bruker), external standard substance: 85% $H_3PO_4$ aqueous solution. mass spectrometry: JMS-700T (manufactured by JEOL Ltd.). elemental analysis: vario EL (manufactured by elementar). melting point: 530 (manufactured by Buchi). polarimeter: P-1030 (manufactured by JASCO).

TOF (mol/mol·h, turnover frequency) was calculated by converting changes in the pressure of hydrogen consumed by the reaction to a substrate conversion ratio, and dividing the amount of the substrate converted in a given time by the amount of the catalyst.

Reference Example 1

(S)-2,2'-bis(trifluoromethanesulfonyloxy)-1,1'-binaphthyl

To a solution of (S)-1,1'-bi-2-naphthol (26.2 g, 91 mmoL) in acetonitrile (130 mL) was added pyridine (19.5 g, 2.7 equivalents) at room temperature. Then, trifluoromethanesulfonic anhydride (64.2 g, 2.5 equivalents) was added to the mixture at 5° C., and the mixture was stirred at 5 to 10° C. for 2 hr. Water (100 mL) was added to the mixture at 3° C., and then ethyl acetate (130 mL) was added to the mixture, and the mixture was stirred at room temperature for 30 min. The reaction mixture was partitioned, and the organic layer was washed with water (50 mL) and concentrated under reduced pressure. Diisopropyl ether (150 mL) and activated carbon (0.25 g) were added to the residue, and the mixture was stirred at 60° C. for 30 min. The activated carbon was removed by filtration, and the filtrate was concentrated under reduced pressure. The residue was recrystallized from heptane to give the title compound (48.9 g, white crystals). yield 97%.

$^1$H-NMR (300 MHz, $CDCl_3$, TMS) δ: 7.33 (d, 2H, J=8.14 Hz), 7.34-7.46 (m, 2H), 7.57-7.63 (m, 2H), 7.68 (d, 2H, J=9.09 Hz), 8.03 (d, 2H, J=8.23 Hz), 8.16 (d, 2H, J=9.08 Hz).

Reference Example 2

4-bromo-N,N,2,6-tetramethylaniline

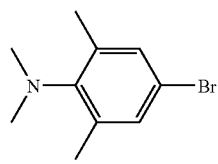

To a solution of 4-bromo-2,6-dimethylaniline (50 g, 0.250 moL) and formic acid (375 g, 32.6 equivalents) was added 37% formaldehyde (50.7 g, 2.5 equivalents) at 23° C., and the mixture was stirred under refluxing for 2 hr. The solvent was evaporated under reduced pressure. Ethyl acetate (200 mL) and 5% aqueous sodium hydrogen carbonate solution (500 mL) were added to the residue, and the mixture was partitioned. The organic layer was successively washed with water (100 mL) and 5% aqueous sodium hydrogen carbonate solution (100 mL). The organic layer was dried over anhydrous magnesium sulfate, and the mixture was filtered naturally. The filtrate was concentrated under reduced pressure and the residue was distilled under reduced pressure to give the title compound (52.0 g, colorless liquid). yield 91%.

$^1$H-NMR (300 MHz, CDCl$_3$, TMS) δ: 2.26 (s, 6H), 2.79 (s, 6H), 7.12 (s, 2H).

Example 1 bis(4-dimethylamino-3,5-dimethylphenyl)phosphine oxide

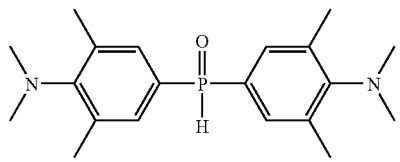

Under an argon atmosphere, a solution of magnesium (2.4 g, 0.75 equivalent), a small amount of iodine and a small amount of 1,2-dibromoethane in tetrahydrofuran (15 mL) was stirred at room temperature for 1 hr. A solution of 4-bromo-N,N,2,6-tetramethylaniline (31.2 g, 0.137 moL) synthesized in Reference Example 2 in tetrahydrofuran (50 mL) was added to the mixture at 25° C. to 30° C. over 1 hr, and the mixture was stirred at 40° C. for 1 hr. Then, a solution of diethyl phosphite (4.69 g, 0.25 equivalent) in tetrahydrofuran (15 mL) was added at 25° C. to 30° C. over 1 hr. Water (60 mL) was added to the mixture at 0° C. to 5° C., and then toluene (100 mL) was added to the mixture, and the insoluble material was removed by filtration. The filtrate was partitioned, and the organic layer was washed with water (30 mL) and concentrated under reduced pressure. The residue was purified by column chromatography (silica gel 100 g, n-hexane/ethyl acetate) to give the title compound (4.6 g, colorless liquid). yield 40%.

$^1$H-NMR (300 MHz, CDCl$_3$, TMS) δ: 2.30 (s, 12H), 2.82 (s, 12H), 7.28 (s, 2H), 7.33 (s, 2H), 7.89 (d, 1H, J=474 Hz).
$^{13}$C-NMR (75 MHz, CDCl$_3$, CDCl$_3$) δ: 19.32, 19.38, 126.09, 127.46, 131.00, 131.17, 132.43, 132.56, 137.09, 137.27, 153.79.
$^{31}$P-NMR (121 MHz, CDCl$_3$, 85% H$_3$PO$_4$) δ: 22.51 (dquint, J=474 Hz, 14 Hz).

Example 2 bis(4-dimethylamino-3,5-dimethylphenyl)phosphine-borane complex

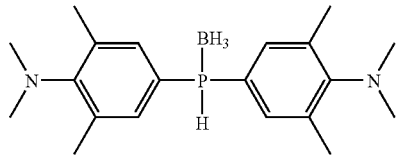

Under an argon atmosphere, to a solution of bis(4-dimethylamino-3,5-dimethylphenyl)phosphine oxide (4.6 g, 14 mmoL) synthesized in Example 1 in toluene (30 mL) was added borane-tetrahydrofuran solution (71 mL, 5.4 equivalents) at room temperature over 2 hr. Then, silica gel (8.7 g, 10.8 equivalents) was added to the mixture, and the mixture was stirred at room temperature for 1.5 hr. The silica gel was removed by filtration, and the filtrate was concentrated under reduced pressure. The residue was purified by column chromatography (silica gel 20 g, toluene) and the residue was recrystallized from n-hexane to give the title compound (3.0 g, white crystals). yield 65%.

$^1$H-NMR (300 MHz, CDCl$_3$, TMS) δ: 0.30-1.75 (m, 3H), 2.28 (s, 12H), 2.81 (s, 12H), 5.44-5.51 (m, 0.5H), 6.70-6.76 (m, 0.5H), 7.23 (s, 2H), 7.28 (s, 2H).
$^{13}$C-NMR (75 MHz, CDCl$_3$, CDCl$_3$) δ: 19.70, 42.69, 121.39, 122.17, 133.62, 133.75, 137.76, 137.9, 153.46.
$^{31}$P-NMR (121 MHz, CDCl$_3$, 85% H$_3$PO$_4$) δ: −2,5--1.5 (m), 0.2-1.2 (m).

Example 3

(S)-2,2'-bis[bis(4-dimethylamino-3,5-dimethylphenyl)phosphino]-1,1'-binaphthyl

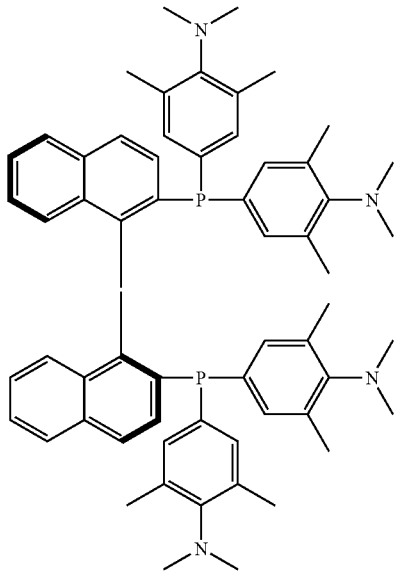

Under an argon atmosphere, to a solution of [1,2-bis(diphenylphosphino)-ethane]dichloronickel (0.17 g, 0.1 equivalent), (S)-2,2'-bis(trifluoromethanesulfonyloxy)-1,1'-binaphthyl (1.76 g, 3.21 mmoL) synthesized in Reference Example 1 and 1,4-diazabicyclo[2,2,2]octane (2.14 g, 6.0 equivalents) in N,N-dimethylformamide (25 mL) was added bis(4-dimethylamino-3,5-dimethylphenyl)phosphine-borane complex (2.52 g, 2.3 equivalents) synthesized in Example 2 at room temperature, and the mixture was stirred at room temperature for 30 min, and at 105° C. for 96 hr. N,N-dimethylformamide was evaporated under reduced pressure, and methanol was added to the residue to give the title compound (1.86 g, white crystals). yield 64%. melting point 265° C. optical rotation: [α]$_D$=−76.5° (25° C., c=1.00, CHCl$_3$).

$^1$H-NMR (300 MHz, CDCl$_3$, TMS) δ: 2.04 (s, 12H), 2.07 (s, 12H), 2.74 (s, 24H), 6.63 (s, 2H), 6.66 (s, 2H), 6.73 (s, 1H), 6.76 (s, 1H), 6.84 (s, 2H), 6.86 (s, 3H), 7.27-7.33 (m, 3H), 7.54-7.58 (m, 2H), 7.78 (s, 1H), 7.83 (s, 1H), 7.86 (s, 1H).
$^{13}$C-NMR (75 MHz, CDCl$_3$, CDCl$_3$) δ: 19.01, 19.03, 42.43, 42.52, 125.03-137.14 (m), 148.94, 149.87.
$^{31}$P-NMR (121 MHz, CDCl$_3$, 85% H$_3$PO$_4$) δ: −15.52 (s).
mass spectrometry (EI-MS)
Found; 905 [M−H]$^+$.

Reference Example 3

4-bromo-2,6-diethyl-N,N-dimethylaniline

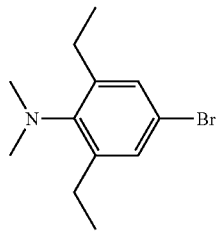

To a solution of 4-bromo-2,6-diethylaniline (30 g, 0.131 mol) and formic acid (196 g, 4.27 mol) was added 37% formaldehyde (26.7 g, 2.5 equivalents) at 37° C., and the mixture was stirred under refluxing for 3 hr. Toluene (100 mL) and 8M aqueous sodium hydroxide solution (150 mL) were added to the mixture at 0° C., the mixture was partitioned, and the organic layer was successively washed with 1M aqueous sodium hydroxide solution (50 mL) and water (50 mL). The organic layer was dried over anhydrous magnesium sulfate and filtered naturally, and the filtrate was concentrated under reduced pressure. The residue was distilled under reduced pressure to give the title compound (29.4 g, slightly yellow liquid). yield 88%.

$^1$H-NMR (300 MHz, CDCl$_3$, TMS) δ: 1.21 (t, 6H, J=7.5 Hz), 2.62 (q, 4H, J=7.5 Hz), 2.80 (s, 6H), 7.16 (s, 2H).

Example 4 bis(4-dimethylamino-3,5-diethylphenyl)phosphine oxide

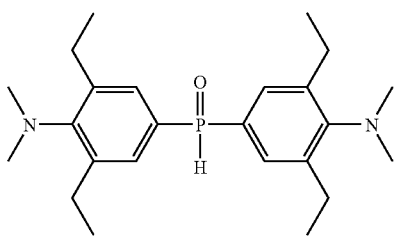

Under an argon atmosphere, a solution of magnesium (2.8 g, 1.0 equivalent), a small amount of iodine and a small amount of 1,2-dibromoethane in tetrahydrofuran (15 mL) was stirred at room temperature for 30 min. A solution of 4-bromo-2,6-diethyl-N, N-dimethylaniline (29.4 g, 0.115 mol) synthesized in Reference Example 3 in tetrahydrofuran (50 mL) was added to the mixture at 20° C. to 25° C. over 1 hr, and the mixture was stirred at 40° C. for 1 hr. Then, a solution of diethyl phosphite (4.01 g, 0.25 equivalent) in tetrahydrofuran (8 mL) was added at 20° C. to 25° C. over 1 hr. Water (90 mL) was added to the mixture at 5° C. to 10° C., and then ethyl acetate (100 mL) was added to the mixture. The mixture was partitioned, and the organic layer was concentrated under reduced pressure. The residue was purified by column chromatography (silica gel 100 g, n-hexane/ethyl acetate) to give the title compound (8.34 g, colorless liquid). yield 72%.

$^1$H-NMR (300 MHz, CDCl$_3$, TMS) δ: 1.20 (t, 12H, J=8 Hz), 2.67 (q, 8H, J=8 Hz), 2.83 (s, 12H), 7.38 (d, 4H, J=14 Hz), 7.98 (d, 1H, J=474 Hz).

$^{13}$C-NMR (75 MHz, CDCl$_3$, CDCl$_3$) δ: 15.18, 15.31, 25.01, 43.31, 43.40, 126.84, 127.01, 128.37, 129.35, 129.51, 131.00, 144.24, 144.42, 152.93, 152.97.

$^{31}$P-NMR (121 MHz, CDCl$_3$, 85% H$_3$PO$_4$) δ: 22.70 (dquint, J=474 Hz, 14 Hz).

mass spectrometry (EI-MS)
Found; 400 [M]$^+$.

Example 5 bis(4-dimethylamino-3,5-diethylphenyl)phosphine-borane complex

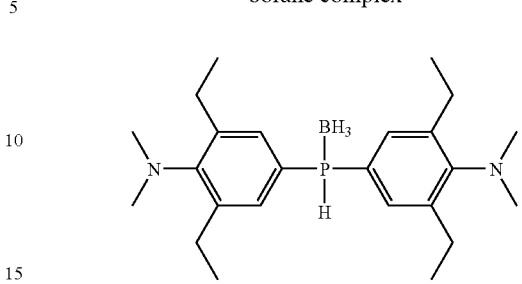

Under an argon atmosphere, to a solution of bis(4-dimethylamino-3,5-diethylphenyl)phosphine oxide (8.12 g, 20 mmol) synthesized in Example 4 in toluene (48 mL) was added borane-tetrahydrofuran solution (68 mL, 3.5 equivalents) at 25° C. to 30° C. over 2 hr. Then, silica gel (8.3 g, 7.0 equivalents) was added to the mixture, and the mixture was stirred at room temperature for 1 hr. The silica gel was removed by filtration, and the filtrate was concentrated under reduced pressure. The residue was purified by column chromatography (silica gel 50 g, toluene) to give the title compound (5.1 g, colorless oil). yield 64%.

$^1$H-NMR (300 MHz, CDCl$_3$, TMS) δ: 0.32-1.65 (m, 3H), 1.20 (t, 12H, J=8 Hz), 2.66 (q, 8H, J=8 Hz), 2.82 (s, 12H), 6.20 (dq, 1H, J=376 Hz, J=7 Hz), 7.34 (d, 4H, J=12 Hz).

$^{13}$C-NMR (75 MHz, CDCl$_3$, CDCl$_3$) δ: 15.24, 24.99, 25.59, 43.33, 67.91, 121.94, 122.71, 131.57, 131.70, 144.44, 144.58, 152.12, 152.16.

$^{31}$P-NMR (121 MHz, CDCl$_3$, 85% H$_3$PO$_4$) δ: −2,6--1.5 (m), 0.2-1.2 (m).

Example 6

(S)-2,2'-bis[bis(4-dimethylamino-3,5-diethylphenyl)phosphino]-1,1'-binaphthyl

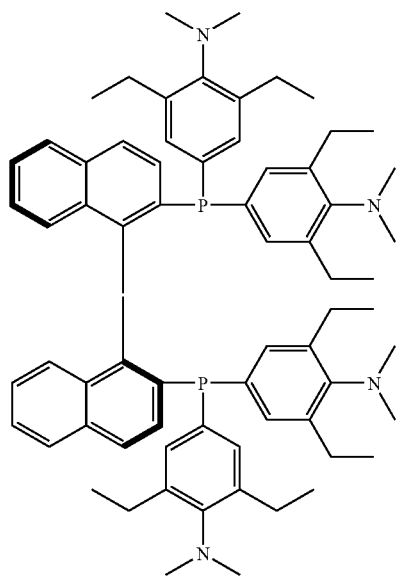

Under an argon atmosphere, to a solution of [1,2-bis(diphenylphosphino)-ethane]dichloronickel (0.28 g, 0.1 equivalent), (S)-2,2'-bis(trifluoromethanesulfonyloxy)-1,1'-binaphthyl (2.93 g, 5 mmoL) synthesized in Reference Example 1 and 1,4-diazabicyclo[2,2,2]octane (3.61 g, 6.0 equivalents) in N,N-dimethylformamide (30 mL) was added bis(4-dimethylamino-3,5-diethylphenyl)phosphine-borane complex (4.79 g, 2.3 equivalents) synthesized in Example 5 at room temperature, and the mixture was stirred at room temperature for 30 min and at 105° C. for 96 hr. N,N-dimethylformamide was evaporated under reduced pressure, and methanol was added to the residue to give the title compound (4.30 g, yellowish white powder). yield 84%. optical rotation: $[\alpha]_D = -32.2°$ (25° C., c=1.01, CHCl$_3$).

$^1$H-NMR (300 MHz, CDCl$_3$, TMS) δ: 1.00 (s, 24H), 2.43-2.45 (m, 16H), 2.74-2.76 (m, 24H), 6.46-8.01 (m, 20H).

$^{13}$C-NMR (75 MHz, CDCl$_3$, CDCl$_3$) δ: 15.48, 24.86, 24.97, 43.62, 43.75, 125.22-148.94(m).

$^{31}$P-NMR (121 MHz, CDCl$_3$, 85% H$_3$PO$_4$) δ: −14.44 (s).

mass spectrometry (FAB-MS)

Found; 1017 [M−H]$^+$, 1019 [M+H]+, 1057 [M+K]$^+$.

Reference Example 4

4-bromo-2,6-diisopropyl-N,N-dimethylaniline

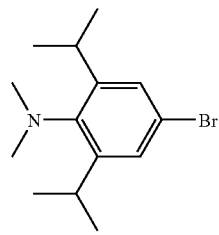 [SMILES: CC(C)c1cc(Br)cc(C(C)C)c1N(C)C]

To a solution of 2,6-diisopropylaniline (25 g, 0.141 moL) in toluene (25 mL) was added dimethyl sulfoxide (12.1 g, 1.1 equivalents), and the mixture was heated to 90° C. 48% Aqueous hydrobromic acid solution (26.1 g, 1.1 equivalents) was added dropwise to the mixture at the same temperature over 30 min. Then, the mixture was stirred at 86° C. for 3 hr and at 100° C. for 2 hr. Water (20 mL) was added to the mixture at 0° C., and 1M aqueous sodium hydroxide solution (30 mL) was added dropwise to the mixture. The mixture was partitioned, and the organic layer was washed with 1M aqueous sodium hydroxide solution (50 mL). The organic layer was dried over anhydrous magnesium sulfate and filtered naturally, and the filtrate was concentrated under reduced pressure. The residue was distilled under reduced pressure to give 4-bromo-2,6-diisopropylaniline (29.4 g, pale-yellow liquid). 37% Formaldehyde (23.1 g, 2.5 equivalents) was added to a solution of 4-bromo-2,6-diisopropylaniline synthesized as mentioned above in formic acid (189 g, 4.11 moL) at 32° C., and the mixture was stirred under refluxing for 2 hr. Toluene (100 mL) and 8M aqueous sodium hydroxide solution (150 mL) were added to the mixture at 0° C., the mixture was partitioned, and the organic layer was successively washed with 1M aqueous sodium hydroxide solution (50 mL) and water (50 mL). The organic layer was dried over anhydrous magnesium sulfate and filtered naturally, and the filtrate was concentrated under reduced pressure. The residue was purified by column chromatography to give the title compound (35.0 g, colorless solid). yield 95%.

$^1$H-NMR (300 MHz, CDCl$_3$, TMS) δ: 1.20 (d, 12H, J=6.9 Hz), 2.82 (s, 6H), 3.31 (septet, 2H, J=6.9 Hz), 7.20 (s, 2H).

Example 7 bis(4-dimethylamino-3,5-diisopropylphenyl)phosphine oxide

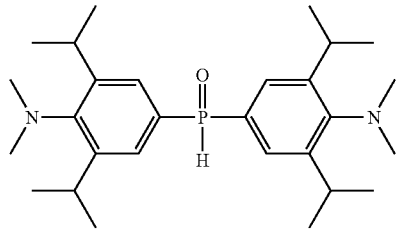

Under an argon atmosphere, a solution of magnesium (2.4 g, 0.75 equivalent), a small amount of iodine and a small amount of 1,2-dibromoethane in tetrahydrofuran (15 mL) was stirred at room temperature for 1 hr. A solution of 4-bromo-2,6-diisopropyl-N,N-dimethylaniline (34.9 g, 0.123 moL) synthesized in Reference Example 4 in tetrahydrofuran (80 mL) was added to the mixture at 25° C. to 35° C. over 1 hr, and the mixture was stirred at 40° C. for 1 hr. Then, a solution of diethyl phosphite (4.23 g, 0.25 equivalent) in tetrahydrofuran (10 mL) was added to the mixture at 20° C. to 25° C. over 1 hr. Water (30 mL) was added to the mixture at 5° C. to 10° C., and ethyl acetate (50 mL) was added to the mixture, and the insoluble material was removed by filtration. Water (30 mL) was added to the filtrate, and ethyl acetate (100 mL) was added thereto. The mixture was partitioned, the organic layer was dried over anhydrous magnesium sulfate and filtered naturally, and then the organic layer was concentrated under reduced pressure. The residue was recrystallized from n-hexane to give the title compound (8.95 g, white solid). yield 63%.

$^1$H-NMR (300 MHz, CDCl$_3$, TMS) δ: 1.19 (dd, J=7 Hz, 1 Hz, 24H), 2.84 (s, 12H), 3.35 (septet, J=6 Hz, 4H), 7.40 (d, J=14 Hz, 4H), 8.02 (d, 1H, J=474 Hz).

$^{13}$C-NMR (75 MHz, CDCl$_3$, CDCl$_3$) δ: 24.14, 24.32, 28.34, 43.71, 43.92, 126.65, 126.81, 127.92, 129.27, 149.89, 150.06, 151.45, 151.49.

$^{31}$P-NMR (121 MHz, CDCl$_3$, 85% H$_3$PO$_4$) δ: 22.93 (dquint, J=474 Hz, 14 Hz).

mass spectrometry (FAB-MS)

Found; 457 [M+H]$^+$, 495 [M+K]$^+$.

Example 8 bis(4-dimethylamino-3,5-diisopropylphenyl)phosphine-borane complex

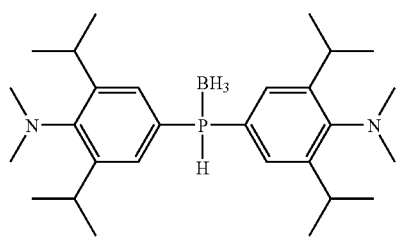

Under an argon atmosphere, to a solution of bis(4-dimethylamino-3,5-diisopropylphenyl)phosphine oxide (8.08 g, 18 mmoL) synthesized in Example 7 in toluene (48 mL) was added borane-tetrahydrofuran solution (60 mL, 3.3 equivalents) at 25° C. to 30° C. over 2 hr. Then, silica gel (7.0 g, 6.3 equivalents) was added to the mixture, and the mixture was stirred at room temperature for 1 hr. Then, silica gel was removed by filtration, and the filtrate was concentrated under reduced pressure. The residue was recrystallized from n-hexane to give the title compound (5.5 g, white crystals). yield 67%.

$^1$H-NMR (300 MHz, CDCl$_3$, TMS) δ: 0.45-1.75 (m, 3H), 1.18 (dd, J=7 Hz, 2 Hz, 24H), 2.83 (s, 12H), 3.33 (septet, J=7 Hz, 4H), 5.57-5.64 (m, 0.5H), 6.82-6.89 (m, 0.5H), 7.34 (d, J=12 Hz, 4H).

$^{13}$C-NMR (75 MHz, CDCl$_3$, CDCl$_3$) δ: 24.14, 24.32, 28.34, 43.71, 43.92, 126.65, 126.81, 127.92, 129.27, 149.89, 150.06, 151.46, 151.49.

$^{31}$P-NMR (121 MHz, CDCl$_3$, 85% H$_3$PO$_4$) δ: −2,6--1.5 (m), 0.5-1.5 (m).

mass spectrometry (FAB-MS)
Found; 453 [M−H]$^+$, 493 [M+K]$^+$.

Example 9

(S)-2,2'-bis[bis(4-dimethylamino-3,5-diisopropylphenyl)phosphino]-1,1'-binaphthyl

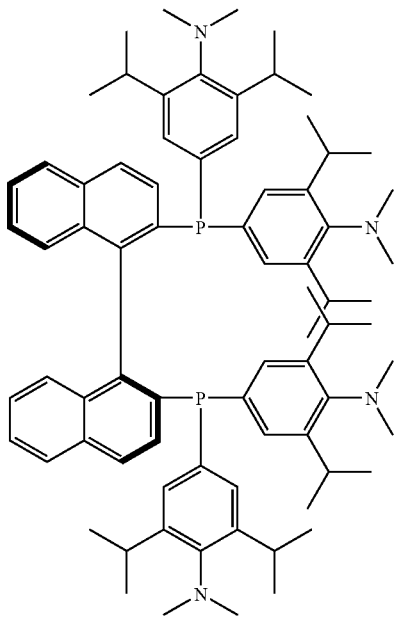

Under an argon atmosphere, to a solution of [1,2-bis(diphenylphosphino)-ethane]dichloronickel (0.25 g, 0.1 equivalent), (S)-2,2'-bis(trifluoromethanesulfonyloxy)-1,1'-binaphthyl (2.63 g, 5.0 mmoL) synthesized in Reference Example 1 and 1,4-diazabicyclo[2,2,2]octane (3.25 g, 6.0 equivalents) in N,N-dimethylformamide (26 mL) was added bis(4-dimethylamino-3,5-diisopropylphenyl)phosphine-borane complex (5.03 g, 2.3 equivalents) synthesized in Example 8 at room temperature, and the mixture was stirred at room temperature for 30 min and at 105° C. for 96 hr. N,N-dimethylformamide was evaporated under reduced pressure, and methanol was added to the residue to give the title compound (2.26 g, reddish white crystals). yield 41%. melting point 265° C. optical rotation: [α]$_D$=−2.70 (25° C., c=1.00, CHCl$_3$).

$^1$H-NMR (300 MHz, CDCl$_3$, TMS) δ: 0.97-1.19 (m, 48H), 2.74-2.85 (m, 24H), 3.10-3.32 (m, 8H), 6.63-7.85 (m, 20H).

$^{13}$C-NMR (75 MHz, CDCl$_3$, CDCl$_3$) δ: 24.07, 24.20, 28.13, 28.31, 44.09, 44.25, 127.52-147.94 (m).

$^{31}$P-NMR (121 MHz, CDCl$_3$, 85% H$_3$PO$_4$) δ: −14.90 (s).

mass spectrometry (FAB-MS)
Found; 1129 [M−H]$^+$, 1131 [M+H]$^+$, 1169 [M+K]$^+$.

Example 10 bis(4-diethylaminophenyl)phosphine oxide

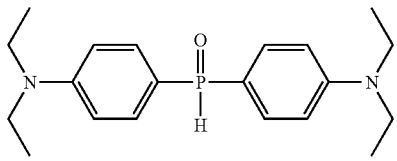

Under a nitrogen stream, a solution of magnesium (5.3 g, 1.00 equivalent), a small amount of iodine and a small amount of 1,2-dibromoethane in tetrahydrofuran (30 mL) was stirred at room temperature for 30 min. A solution of 4-bromo-N,N-diethylaniline (49.7 g, 0.217 moL) in tetrahydrofuran (100 mL) was added to the mixture at 25° C. to 35° C. over 1 hr, and the mixture was stirred at 40° C. for 40 min. Then, a solution of diethyl phosphite (9.20 g, 0.30 equivalent) in tetrahydrofuran (20 mL) was added to the mixture at 20° C. to 25° C. for 15 min. 6M Hydrochloric acid (30 mL) and water (30 mL) were added to the mixture at 3° C. to 15° C., and then ethyl acetate (100 mL) was added thereto. The mixture was partitioned, and the organic layer was washed successively with water (30 mL), 5%-aqueous sodium hydrogen carbonate solution (30 mL) and saturated brine (30 mL), dried over anhydrous magnesium sulfate and filtered naturally. Then, the organic layer was concentrated under reduced pressure. The residue was recrystallized from n-heptane to give the title compound (19.82 g, white crystals). yield 87%. melting point 129.1° C.

$^1$H-NMR (300 MHz, CDCl$_3$, TMS) δ: 1.16 (t, J=7 Hz, 12H), 3.28 (q, J=7 Hz, 8H), 6.67 (dd, J=2 Hz, 6 Hz, 4H), 7.47 (dd, J=13 Hz, 9 Hz, 4H), 7.93 (d, J=468 Hz, 1H).

$^{13}$C-NMR (75 MHz, CDCl$_3$, CDCl$_3$) δ: 12.82, 44.71, 111.20, 111.37, 116.02, 117.51, 132.79, 132.96, 150.66, 150.68.

$^{31}$P-NMR (121 MHz, CDCl$_3$, 85% H$_3$PO$_4$) δ: 22.70 (dquint, J=468 Hz, 13 Hz).

mass spectrometry (FAB-MS)
Found; 345 [M+H]$^+$, 367 [M+Na]$^+$, 383 [M+K]$^+$.

Example 11 bis(4-diethylaminophenyl)phosphine-borane complex

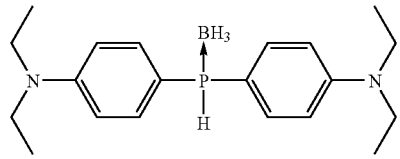

Under a nitrogen stream, to a solution of bis(4-diethylaminophenyl)phosphine oxide (3.76 g, 10 mmoL) synthesized in Example 10 in tetrahydrofuran (35 mL) was added borane-tetrahydrofuran solution (35 mL, 3.3 equivalents) at 25° C. to 30° C. over 2 hr. Then, silica gel (6.3 g, 9.7 equivalents) was added to the mixture, and the mixture was stirred at room temperature for 3 hr. Then, silica gel was removed by filtration, and the filtrate was concentrated under reduced pressure. The residue was recrystallized from n-hexane/ethyl acetate (1/1) to give the title compound (1.8 g, white crystals). yield 49%. melting point 108.5° C.

$^1$H-NMR (300 MHz, CDCl$_3$, TMS) δ: 0.50-1.50 (m, 3H), 1.14 (t, J=7 Hz, 12H), 3.34 (q, J=7 Hz, 8H), 5.53-5.59 (m, 0.5H), 6.62-6.66 (m, 4H), 6.77-6.84 (m, 0.5H), 7.41-7.48 (m, 4H).
$^{13}$C-NMR (75 MHz, CDCl$_3$, CDCl$_3$) δ: 12.42, 44.28, 109.64, 110.52, 111.27, 111.42, 134.12, 134.26, 149.62.
$^{31}$P-NMR (121 MHz, CDCl$_3$, 85% H$_3$PO$_4$) δ: −7.7-−4.7 (m), −4,6-−1.7 (m).
mass spectrometry (FAB-MS)
Found; 341 [M−H]$^+$, 343 [M+H]$^+$, 365 [M+Na]$^+$. 381 [M+K]$^+$.

Example 12

(S)-2,2'-bis[bis(4-diethylaminophenyl)phosphino]-1,1'-binaphthyl

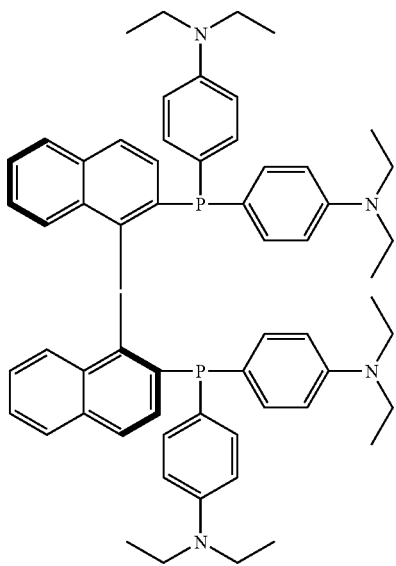

Under an argon atmosphere, to a solution of [1,2-bis(diphenylphosphino)-ethane]dichloronickel (0.13 g, 0.1 equivalent), (S)-2,2'-bis(trifluoromethanesulfonyloxy)-1,1'-binaphthyl (1.31 g, 2.3 mmoL) synthesized in Reference Example 1 and 1,4-diazabicyclo[2,2,2]octane (1.60 g, 6.0 equivalents) in N,N-dimethylformamide (15 mL) was added bis(4-diethylaminophenyl)phosphine-borane complex (1.86 g, 2.3 equivalents) synthesized in Example 11 at room temperature, and the mixture was stirred at room temperature for 30 min and at 105° C. for 114 hr. N,N-Dimethylformamide was evaporated under reduced pressure, and methanol was added to the residue to give the title compound (0.49 g, dark gray powder). yield 23%. optical rotation: [α]$_D$=−22.8° (25° C., c=0.20, CHCl$_3$).

$^1$H-NMR (300 MHz, CDCl$_3$, TMS) δ: 1.07-1.16 (m, 24H), 3.21-3.36 (m, 16H), 6.30-7.92 (m, 28H).

$^{13}$C-NMR (75 MHz, CDCl$_3$, CDCl$_3$) δ: 13.10, 13.13, 44.66, 111.68, 112.09, 125.42, 125.85, 127.74, 127.99, 128.19, 130.84, 133.34, 133.94, 134.72, 134.85, 135.00, 136.17, 136.32, 136.48, 148.02.
$^{31}$P-NMR (121 MHz, CDCl$_3$, 85% H$_3$PO$_4$) δ: −17.86 (s).
mass spectrometry (EI-MS)
Found; 906 [M$^+$], 905 [M−H]$^+$.

Reference Example 5

N-(4-bromophenyl)pyrrolidine

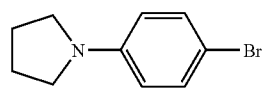 [SMILES: Brc1ccc(N2CCCC2)cc1]

To a solution of N-phenylpyrrolidine (73.8 g, 0.501 moL) in tetrahydrofuran (500 mL) was added N-bromosuccinimide (124.8 g, 1.4 equivalents) at 20° C. to 30° C., and the mixture was stirred at the same temperature for 4 hr. 1 mol/L Aqueous sodium hydroxide solution (300 mL) was added to the mixture at 27° C., and the mixture was partitioned. The organic layer was dried over anhydrous magnesium sulfate and filtered naturally, and the filtrate was concentrated under reduced pressure. The residue was recrystallized from methanol to give the title compound (97.4 g, brown crystals). yield 86%. melting point 88.1° C.

$^1$H-NMR (300 MHz, CDCl$_3$, TMS) δ: 1.94-2.02 (m, 4H), 3.19-3.26 (m, 4H), 6.39 (d, J=8 Hz, 2H), 7.25 (d, J=8 Hz, 2H).
$^{13}$C-NMR (75 MHz, CDCl$_3$, CDCl$_3$) δ: 25.95, 48.14, 113.66, 132.15.
mass spectrometry (EI-MS)
Found; 225 [M]$^+$, 224 [M−H]$^+$.

Example 13 bis[4-(pyrrolidin-1-yl)phenyl]phosphine oxide

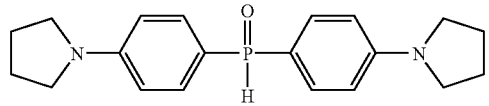

Under a nitrogen stream, a solution of magnesium (9.7 g, 1.0 equivalent), a small amount of iodine and a small amount of 1,2-dibromoethane in tetrahydrofuran (60 mL) was stirred at room temperature for 30 min. A solution of N-(4-bromophenyl)pyrrolidine (90.5 g, 0.400 moL) synthesized in Reference Example 5 in tetrahydrofuran (200 mL) was added at 20° C. to 40° C. over 1 hr, and the mixture was stirred at 40° C. for 40 min. Then, a solution of diethyl phosphite (16.80 g, 0.30 equivalent) in tetrahydrofuran (40 mL) was added to the mixture at 20° C. to 30° C. over 15 min. 6M Hydrochloric acid (60 mL) and water (60 mL) were added to the mixture at −15° C. to 10° C., and then ethyl acetate (200 mL) and acetone (100 mL) were added thereto. The mixture was partitioned, and the organic layer was washed twice with saturated brine (60 mL), dried over anhydrous magnesium sulfate and filtered naturally. Then, the organic layer was concentrated under reduced pressure. The residue was recrystallized from ethyl acetate to give the title compound (2.91 g, pale-yellow white crystals). yield 7%. melting point 199.0° C.

$^1$H-NMR (300 MHz, CDCl$_3$, TMS) δ: 1.98-2.02 (m, 8H), 3.28-3.32 (m, 8H), 6.54-6.57 (m, 4H), 7.44-7.51 (m, 4H), 7.95 (d, J=468 Hz, 1H).

$^{13}$C-NMR (75 MHz, CDCl$_3$, CDCl$_3$) δ: 25.84, 47.84, 111.64, 111.82, 116.26, 117.76, 132.68, 132.85, 150.57.

$^{31}$P-NMR (121 MHz, CDCl$_3$, 85% H$_3$PO$_4$) δ: 23.28 (dquint, J=468 Hz, 13 Hz).

mass spectrometry (FAB-MS)
Found; 340 [M]$^+$, 339 [M−H]$^+$.

Example 14 bis[4-(pyrrolidin-1-yl)phenyl]phosphine-borane complex

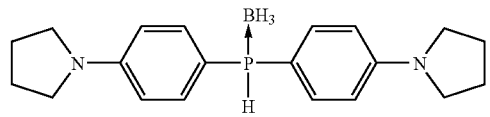

Under a nitrogen stream, to a solution of bis[4-(pyrrolidin-1-yl)phenyl]phosphine oxide (2.50 g, 7.34 mmoL) synthesized in Example 13 in tetrahydrofuran (25 mL) was added borane-tetrahydrofuran solution (29 mL, 3.9 equivalents) at 25° C. to 30° C. over 2.4 hr. Then, silica gel (10.0 g, 22.6 equivalents) was added to the mixture, and the mixture was stirred at room temperature for 1 hr. Silica gel was removed by filtration, and the filtrate was concentrated under reduced pressure. The residue was purified by column chromatography (silica gel 25 g, dichloromethane) to give the title compound (0.7 g, white crystals). yield 27%. melting point 178.3° C.

$^1$H-NMR (300 MHz, CDCl$_3$, TMS) δ: 0.35-1.55 (m, 3H), 1.90-2.03 (m, 8H), 3.23-3.30 (m, 8H), 5.55-5.61 (m, 0.5H), 6.52-6.55 (m, 4H), 6.79-6.86 (m, 0.5H), 7.42-7.48 (m,4H).

$^{13}$C-NMR (75 MHz, CDCl$_3$, CDCl$_3$) δ: 25.43, 47.42, 110.01, 110.89, 111.69, 111.84, 133.97, 134.11, 149.61. $^{31}$P-NMR (121 MHz, CDCl$_3$, 85% H$_3$PO$_4$) δ: −6,7--4.7 (m), −3,1--1.1 (m).

mass spectrometry (FAB-MS)
Found; 338 [M]$^+$, 337 [M−H]$^+$.

Example 15

(S)-2,2'-bis[bis[4-(pyrrolidin-1-yl)phenyl]phosphino]-1,1'-binaphthyl

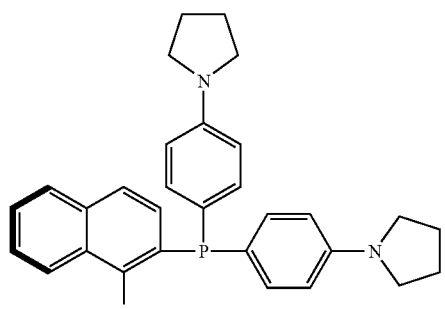

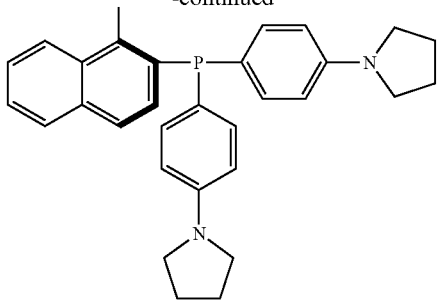

Under an argon atmosphere, to a solution of [1,2-bis(diphenylphosphino)-ethane]dichloronickel (34.3 mg, 0.1 equivalent), (S)-2,2'-bis(trifluoromethanesulfonyloxy)-1,1'-binaphthyl (358.9 mg, 0.65 mmoL) synthesized in Reference Example 1 and 1,4-diazabicyclo[2,2,2]octane (440.5 mg, 6.0 equivalents) in N,N-dimethylformamide (4 mL) was added bis[4-(pyrrolidin-1-yl)phenyl]phosphine-borane complex (512.0 mg, 2.3 equivalents) synthesized in Example 14 at room temperature, and the mixture was stirred at room temperature for 30 min and at 105° C. for 127 hr. N,N-Dimethylformamide was evaporated under reduced pressure, and methanol was added to the residue to give the title compound (367.0 mg, dark gray powder). yield 62%. optical rotation: [α]$_D$=−185° (25° C., c=0.20, CHCl$_3$).

$^1$H-NMR (300 MHz, CDCl$_3$, TMS) δ: 1.91-2.00 (m, 16H), 3.20-3.30 (m, 16H), 6.26-7.83 (m,28H).

$^{13}$C-NMR (75 MHz, CDCl$_3$, CDCl$_3$) δ: 25.90, 47.88, 111.80, 111.85, 111.99, 125.69, 126.13, 127.91, 128.18, 131.03, 133.44, 134.48, 134.62, 134.76, 136.12, 147.56, 148.18.

$^{31}$P-NMR (121 MHz, CDCl$_3$, 85% H$_3$PO$_4$) δ: −17.45 (s).

mass spectrometry (FAB-MS)
Found; 898 [M]$^+$, 897 [M−H]$^+$.

Example 16

Synthesis of dichloro{(S)-2,2'-bis[bis(4-dimethylamino-3,5-dimethylphenyl)phosphino]-1,1'-binaphthyl}ruthenium (II)-N,N-dimethylformamide complex

[RuCl$_2$(L)(dmf)$_n$] L=(S)-2,2'-bis[bis(4-dimethylamino-3,5-dimethylphenyl)phosphino]-1,1'-binaphthyl Under an argon atmosphere, to di-μ-chlorobis[η$^6$-benzene)chlororuthenium (II)] (100.9 mg, 0.202 mmoL) and (S)-2,2'-bis[bis(4-dimethylamino-3,5-dimethylphenyl)phosphino]-1,1'-binaphthyl (379.5 mg, 0.418 mmoL) synthesized in Example 3 was added N,N-dimethylformamide (4 mL), and the mixture was stirred at 150° C. for 1 hr. The solvent was evaporated under reduced pressure to give the title compound (0.52 g, red-brown powder).

$^{31}$P-NMR (121 MHz, CD$_2$Cl$_2$, 85% H$_3$PO$_4$) δ: 26.3(s), 27.0(s), 34.1(d, J=28 Hz), 44.8(d, J=28 Hz), 48.2(d, J=36 Hz), 64.2(s), 71.5(s).

Example 17

Synthesis of diacetato{(S)-2,2'-bis[bis(4-dimethylamino-3,5-dimethylphenyl)phosphino]-1,1'-binaphthyl}ruthenium (II)

[Ru(OAc)$_2$(L)] L=(S)-2,2'-bis[bis(4-dimethylamino-3,5-dimethylphenyl)phosphino]-1,1'-binaphthyl Under an argon atmosphere, to dichloro{(S)-2,2'-bis[bis(4-dimethylamino-3,5-dimethylphenyl)phosphino]-1,1'-binaphthyl}ruthenium (II)-N,N-dimethylformamide complex (502.2 mg, 0.435 mmoL) synthesized in Example 16 was added a solution of sodium acetate (637.3 mg, 7.77 mmoL) in methanol (6 mL), and the mixture was ultrasonicated and allowed to react for 20 min. Toluene (6 mL) and water (6 mL) were added to the reaction mixture, and the mixture was partitioned. Water (6 mL) was further added to the organic layer, and the mixture was partitioned. The solvent of the organic layer was evaporated, and the residue was recrystallized from a toluene/n-hexane mixed solvent to give the title compound (256 mg, orange powder). yield 62%.

$^1$H-NMR (300 MHz, CD$_2$Cl$_2$, CD$_2$Cl$_2$) δ: 1.77 (s, 12H), 1.85 (s, 6H), 2.34 (s, 12H), 2.52 (s, 12H), 2.90 (s, 12H), 6.6-6.7 (m, 4H), 6.7-6.8 (m, 2H), 6.9-7.1 (m, 2H), 7.2-7.3 (m, 2H), 7.3-7.4 (m, 2H), 7.5-7.6 (m, 2H), 7.6-7.7 (m, 2H).
$^{13}$C-NMR (75 MHz, CD$_2$Cl$_2$, CD$_2$Cl$_2$) δ: 13.8, 18.7, 19.4, 22.6, 23.2, 31.5, 42.2, 124.5, 126.1, 126.6, 127.2, 127.3, 127.6, 128.1, 128.2, 128.6, 128.9, 129.8, 130.1, 130.4, 132.8, 133.0, 134.0, 134.1, 134.2, 135.4, 135.5, 135.6, 135.7, 138.2, 149.8, 150.9, 187.2.
$^{31}$P-NMR (121 MHz, CD$_2$Cl$_2$, 85% H$_3$PO$_4$) δ: 61.4 (s).

Example 18

Synthesis of η$^6$-benzene chloro{(S)-2,2'-bis[bis(4-dimethylamino-3,5-dimethylphenyl)phosphino]-1,1'-binaphthyl}ruthenium (II) chloride

[RuCl(benzene)(L)]Cl L=(S)-2,2'-bis[bis(4-dimethylamino-3,5-dimethylphenyl)phosphino]-1,1'-binaphthyl Under an argon atmosphere, to di-μ-chlorobis[η$^6$-benzene)chlororuthenium (II)] (99.1 mg, 0.198 mmoL) and (S)-2,2'-bis[bis(4-dimethylamino-3,5-dimethylphenyl)phosphino]-1,1'-binaphthyl (365.6 mg, 0.403 mmoL) synthesized in Example 3 were added ethanol (45 mL) and benzene (6 mL), and the mixture was stirred at 55° C. for 1 hr. After the mixture was cooled to room temperature, the insoluble material was removed by filtration, and the filtrate was evaporated under reduced pressure to give the title compound (430 mg, brown powder). yield 93%.

$^{31}$P-NMR (121 MHz, CD$_2$Cl$_2$, 85% H$_3$PO$_4$) δ: 27.3 (d, J=62.2 Hz), 34.5 (d, J=62.4 Hz).

Example 19

Synthesis of {(S)-2,2'-bis[bis(4-dimethylamino-3,5-dimethylphenyl)phosphino]-1,1'-binaphthyl}bis(η$^3$-2-methylallyl)ruthenium (II)

[Ru(2-methylallyl)$_2$(L)] L=(S)-2,2'-bis[bis(4-dimethylamino-3,5-dimethylphenyl)phosphino]-1,1'-binaphthyl Under an argon atmosphere, to (η$^2$,η$^2$-1,5-cyclooctadiene)bis(η$^3$-2-methylallyl)ruthenium (II) (160.8 mg, 0.503 mmoL) and (S)-2,2'-bis[bis(4-dimethylamino-3,5-dimethylphenyl)phosphino]-1,1'-binaphthyl (452.4 mg, 0.499 mmoL) synthesized in Example 3 was added toluene (2 mL), and the mixture was stirred at 110° C. for 5 hr. After cooling to room temperature, the reaction mixture was evaporated under reduced pressure. The residue was washed with toluene (1 mL) and n-hexane (5 mL) to give the title compound (80 mg, yellow powder). yield 14%.

$^1$H-NMR (300 MHz, CD$_2$Cl$_2$, CD$_2$Cl$_2$) δ: 1.51 (s, 2H), 1.70 (s, 12H), 2.17 (s, 6H), 2.23 (s, 12H), 2.27 (s, 4H), 2.30-2.50 (m, 14H), 2.82 (s, 12H), 6.2-6.3 (m, 4H), 7.1-7.3 (m, 4H), 7.3-7.4 (m, 2H), 7.5-7.6 (m, 10H).
$^{13}$C-NMR (75 MHz, CD$_2$Cl$_2$, CD$_2$Cl$_2$) δ: 13.7, 18.8, 18.9, 24.1, 37.4, 41.5, 41.9, 42.2, 93.7, 124.3, 125.3, 125.4, 127.1, 128.1, 130.2, 132.2, 132.6, 132.9, 134.1, 134.7, 136.2, 137.0, 143.2, 148.8, 149.5.
$^{31}$P-NMR (121 MHz, CD$_2$Cl$_2$, 85% H$_3$PO$_4$) δ: 34.5 (s).

Example 20

Asymmetric hydrogenation of 1-(3,5-bis(trifluoromethyl)phenyl)-ethanone

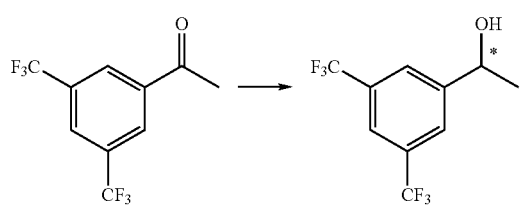 [SMILES: CC(=O)c1cc(C(F)(F)F)cc(C(F)(F)F)c1 ; CC(O)c1cc(C(F)(F)F)cc(C(F)(F)F)c1]

To a solution of dichloro{(S)-2,2'-bis[bis(4-dimethylamino-3,5-dimethylphenyl)phosphino]-1,1'-binaphthyl}ruthenium (II)-N,N-dimethylformamide complex (2.2 mg, 0.00195 mmoL) synthesized in Example 16, (2S)-(+)-1,1-bis(4-methoxyphenyl)-3-methyl-1,2-butanediamine (2.4 mg, 0.0078 mmoL) and potassium tert-butoxide (1.7 mg, 0.0156 mmoL) in 2-propanol (1 mL) was added a solution of 1-(3,5-bis(trifluoromethyl)phenyl)-ethanone (0.05 g, 0.195 mmoL) in 2-propanol (1 mL). The mixture was subjected to hydrogenation under a 1.0 MPa hydrogen pressure at 25° C. for 12 hr. The reaction mixture was analyzed by GC (column: CHIRASIL-DEX CB, 0.32 mm×25 m) to find a conversion ratio of 99.6% and an optical purity of 94.6% ee(R).

Comparative Example 1

Asymmetric hydrogenation of 1-(3,5-bis(trifluoromethyl)phenyl)-ethanone

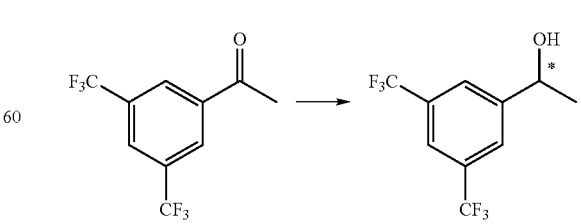

To a solution of dichloro[(S)-2,2'-bis(diphenylphosphino)-1,1'-binaphthyl]ruthenium (II)-N,N-dimethylformamide complex (1.7 mg, 0.00195 mmoL) synthesized in the same method as in Example 16, (2S)-(+)-1,1-bis(4-methoxyphenyl)-3-methyl-1,2-butanediamine (2.4 mg, 0.0078 mmol) and potassium tert-butoxide (1.7 mg, 0.0156 mmoL) in 2-propanol (1 mL) was added a solution of 1-(3,5-bis(trifluoromethyl)phenyl)-ethanone (0.05 g, 0.195 mmoL) in 2-propanol (1 mL). The mixture was subjected to hydrogenation under a 1.0 MPa hydrogen pressure at 25° C. for 12 hr. The reaction mixture was analyzed by GC (column: CHIRASIL-DEX CB, 0.32 mm×25 m) to find a conversion ratio of 60.8% and an optical purity of 62.9% ee(R).

Example 21

Asymmetric hydrogenation of 2-(6-methoxy-3,4-dihydro-naphthalen-2-yl)-N,N-dimethyl-acetamide

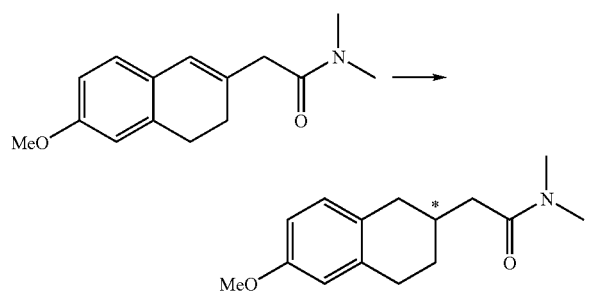

A solution of diacetato{(S)-2,2'-bis[bis(4-dimethylamino-3,5-dimethylphenyl)phosphino]-1,1'-binaphthyl}ruthenium (II) (9.2 mg, 0.00817 mmoL) synthesized in Example 17 and 2-(6-methoxy-3,4-dihydro-naphthalen-2-yl)-N,N-dimethyl-acetamide (5.0114 g, 20.42 mmoL) in ethanol (40 mL) was stirred at room temperature for 10 min. The mixture was subjected to hydrogenation under a 1.0 MPa hydrogen pressure at 25° C. TOF (moL/moL·h, turnover frequency) was 1538. The reaction mixture was analyzed by HPLC (column: CHIRALCEL-OD, 4.6 mm×25 cm) to find a conversion ratio of 99.9% and an optical purity of 98.1% ee(+).

Comparative Example 2

Asymmetric hydrogenation of 2-(6-methoxy-3,4-dihydro-naphthalen-2-yl)-N,N-dimethyl-acetamide

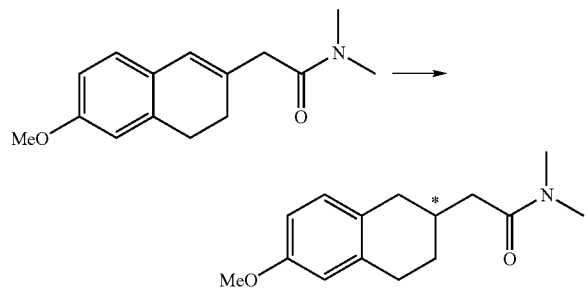

A solution of diacetato{(S)-2,2'-bis[bis(3,5-dimethylphenyl)phosphino]-1,1'-binaphthyl}ruthenium (II) (10.2 mg, 0.01069 mmoL) synthesized in the same method as in Example 17 and 2-(6-methoxy-3,4-dihydro-naphthalen-2-yl)-N,N-dimethyl-acetamide (5.0332 g, 20.52 mmoL) in ethanol (40 mL) was stirred at room temperature for 10 min. The mixture was subjected to hydrogenation under a 1.0 MPa hydrogen pressure at 25° C. TOF (moL/moL·h, turnover frequency) was 844. The reaction mixture was analyzed by HPLC (column: CHIRALCEL-OD, 4.6 mm×25 cm) to find a conversion ratio of 99.9% and an optical purity of 98.4% ee(+).

Reference Example 6 bis(4-dimethylaminophenyl)phosphine oxide

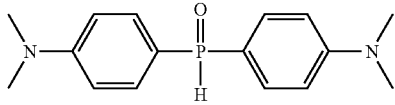

Under an argon atmosphere, a solution of magnesium (3.0 g, 1.0 equivalent) and a small amount of iodine in tetrahydrofuran (30 mL) was stirred at room temperature for 1 hr. After addition of 4-bromo-N,N-dimethylaniline (25 g, 0.125 moL) at 45° C., the mixture was stirred at 5° C. for 1 hr. After addition of diethyl phosphite (8.63 g, 0.50 equivalent) at 5° C., the mixture was stirred at 5° C. for 1 hr. Water (30 mL) was added to the mixture at 3° C., and toluene (60 mL) and 6M hydrochloric acid (30 mL) were added thereto, and the mixture was stirred at room temperature for 30 min. The reaction mixture was partitioned, and the aqueous layer was neutralized with sodium hydroxide and extracted with tetrahydrofuran (30 mL). Then, the combined organic layer was dried over anhydrous magnesium sulfate and filtered naturally, and the filtrate was concentrated under reduced pressure. The residue was recrystallized from diisopropyl ether to give the title compound (9.53 g, slightly brown white crystals). yield 52.9%. melting point 152.1° C.

$^1$H-NMR (300 MHz, CDCl$_3$, TMS) δ: 3.01 (s, 12H), 6.71 (d, 2H, J=8.94 Hz), 6.72 (d, 2H, J=8.94 Hz), 7.48 (d, 2H, J=8.91 Hz), 7.52 (d, 2H, J=8.88 Hz), 7.96 (d, 1H, J=470.1 Hz).

$^{31}$P-NMR (121 MHz, CDCl$_3$, 85% H$_3$PO$_4$) δ: 22.78 (dquint, J=469.2 Hz, 12.7 Hz).

elemental analysis for C$_{16}$H$_{21}$N$_2$OP
Calcd.; C, 66.65; H, 7.34; N, 9.72, P, 10.74.
Found; C, 66.56; H, 7.43; N, 9.57, P, 10.79.

Reference Example 7 bis(4-dimethylaminophenyl)phosphine-borane complex

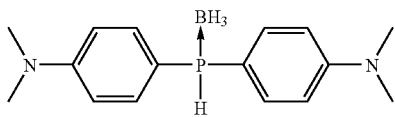

Under an argon atmosphere, a solution of cerium chloride (7.69 g, 3.0 equivalents) in tetrahydrofuran (25 mL) was stirred at room temperature (25° C.) for 30 min. After addition of sodium borohydride (1.22 g, 3.1 equivalents), the mixture was stirred at room temperature for 1 hr. After bis(4-dimethylaminophenyl)phosphine oxide (3.0 g, 10.4 mmoL) synthesized in Reference Example 6 and lithium aluminum hydride (0.47 g, 1.2 equivalents) were successively added to the mixture at 5° C., the mixture was stirred at room temperature for 3 hr. Water (20 mL) was added to the mixture at 3° C., and then toluene (40 mL) and 6M hydrochloric acid (10 mL) were added thereto, and the mixture was stirred at room temperature for 30 min. The reaction mixture was neutralized with sodium hydroxide, and the mixture was partitioned. The aqueous layer was extracted with tetrahydrofuran (50 mL). The combined organic layer was successively washed with 5% brine (20 mL). The organic layer was dried over anhydrous magnesium sulfate and filtered naturally, and the filtrate was concentrated under reduced pressure. The residue was purified by column chromatography (silica gel 5 g, n-hexane/ethyl acetate=1/1). The residue was recrystallized from n-heptane to give the title compound (0.61 g, white crystals). yield 20.5%. melting point 142.6° C.

$^1$H-NMR (300 MHz, CDCl$_3$, TMS) δ: 0.43-1.33 (m, 3H), 3.03 (s, 12H), 6.26 (dq, 1H, J=375.1 Hz, 6.57 Hz), 7.51 (d, 4H, J=8.81 Hz), 7.54 (d, 4H, J=8.81 Hz).
$^{31}$P-NMR (121 MHz, CDCl$_3$, 85% H$_3$PO$_4$) δ: −6.40−−4.73 (m), −3.33−−1.66 (m).

Reference Example 8

(S)-2,2'-bis[bis(4-dimethylaminophenyl)phosphino]-1,1'-binaphthyl

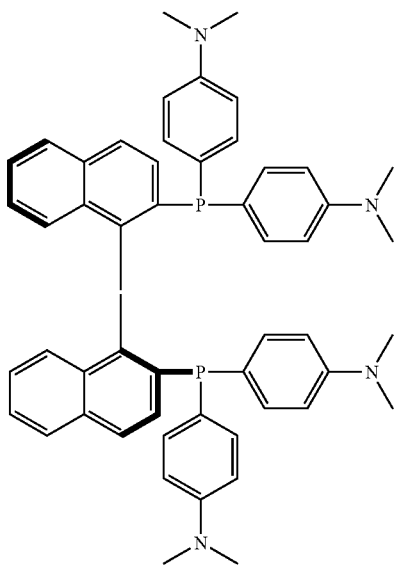

Under an argon atmosphere, to a solution of [1,2-bis(diphenylphosphino)-ethane]dichloronickel (48 mg, 0.1 equivalent), (S)-2,2'-bis(trifluoromethanesulfonyloxy)-1,1'-binaphthyl (507 mg, 0.92 mmol) synthesized in Reference Example 1 and 1,4-diazabicyclo[2,2,2]octane (620 mg, 6.0 equivalents) in N,N-dimethylformamide (5 mL) was added bis(4-dimethylaminophenyl)phosphine-borane complex (606 mg, 2.3 equivalents) synthesized in Reference Example 7 at room temperature, and the mixture was stirred at room temperature for 30 min and at 110° C. for 129 hr. N,N-Dimethylformamide was evaporated under reduced pressure, and methanol was added to the residue to give the title compound (461 mg, yellow-white crystals). yield 62.9%.

$^1$H-NMR (300 MHz, CDCl$_3$, TMS) δ: 2.88 (s, 24H), 6.43 (d, 4H, J=6.79 Hz), 6.50-6.59 (m, 4H), 6.77-7.03 (m, 12H), 7.18-7.26 (m, 2H), 7.51 (d, 2H, J=7.13 Hz), 7.78 (d, 2H, J=7.56 Hz), 7.83 (d, 2H, J=8.28 Hz).
$^{31}$P-NMR (121 MHz, CDCl$_3$, 85% H$_3$PO$_4$) δ: −18.00 (s).

Example 22

Synthesis of dichloro{(S)-2,2'-bis[bis(4-dimethylaminophenyl)phosphino]-1,1'-binaphthyl}ruthenium (II)-N,N-dimethylformamide complex

[RuCl$_2$(L)(dmf)] L=(S)-2,2'-bis[bis(4-dimethylaminophenyl)phosphino]-1,1'-binaphthyl Under an argon atmosphere, to di-µ-chlorobis[(η$^6$-benzene)chlororuthenium (II)] (99.9 mg, 0.1997 mmol) and (S)-2,2'-bis[bis(4-dimethylaminophenyl)phosphino]-1,1'-binaphthyl (319.2 mg, 0.4015 mmol) synthesized in Reference Example 8 was added N,N-dimethylformamide (6 mL), and the mixture was stirred at 120° C. for 1 hr. Then, the solvent was evaporated under reduced pressure to give the title compound (0.485 g).
$^{31}$P-NMR (121 MHz, CD$_2$Cl$_2$, 85% H$_3$PO$_4$) δ: 44.4(s), 63.4(s), 73.5(s), 74.4(s).

Example 23

Synthesis of diacetato{(S)-2,2'-bis[bis(4-dimethylaminophenyl)phosphino]-1,1'-binaphthyl}ruthenium (II)

[Ru(OAc)$_2$(L)] L=(S)-2,2'-bis[bis(4-dimethylaminophenyl)phosphino]-1,1'-binaphthyl Under an argon atmosphere, to dichloro{(S)-2,2'-bis(4-dimethylaminophenyl)phosphino]-1,1'-binaphthyl}ruthenium (II)-N,N-dimethylformamide complex (105.9 mg, 0.102 mmol) synthesized in Example 22 was added a solution of sodium acetate (320.1 mg, 3.9 mmol) in methanol (5 mL), and the mixture was ultrasonicated to allow reaction for 20 min. Toluene (5 mL) and water (5 mL) were added to the reaction mixture, and the mixture was partitioned. Toluene (5 mL) was added to the aqueous layer, and the mixture was partitioned. Water (5 mL) was added to all organic layers, and the mixture was partitioned. The solvent of the organic layer was evaporated and the residue was recrystallized from toluene/n-hexane (10 mL) to give the title compound (40.2 mg, brown powder).
$^{31}$P-NMR (121 MHz, CD$_2$Cl$_2$, 85% H$_3$PO$_4$) δ: 60.6 (s).

Example 24

Synthesis of dichloro{(S)-2,2'-bis[bis(4-dimethylamino-3,5-diethylphenyl)phosphino]-1,1'-binaphthyl}ruthenium (II)-N,N-dimethylformamide complex

[RuCl$_2$(L)(dmf)$_n$] L=(S)-2,2'-bis[bis(4-dimethylamino-3,5-diethylphenyl)phosphino]-1,1'-binaphthyl Under an argon atmosphere, to di-µL-chlorobis[(η$^6$-benzene)chlororuthenium (II)] (152.2 mg, 0.3043 mmol) and (S)-2,2'-bis[bis(4-dimethylamino-3,5-diethylphenyl)phosphino]-1,1'-binaphthyl (616.0 mg, 0.604 mmol) synthesized in Example 6 was added N,N-dimethylformamide (6 mL), and the mixture was stirred at 120° C. for 3.5 hr. Then, the solvent was evaporated under reduced pressure to give the title compound (0.7905 g).
$^{31}$P-NMR (121 MHz, $CD_2Cl_2$, 85% $H_3PO_4$) δ: 31.7(s), 39.9(d, J=26.1 Hz), 46.2(d, J=26.5 Hz), 50.2(q), 51.2(s), 66.7(s), 68.1(s).

Example 25

Synthesis of diacetato{(S)-2,2'-bis[bis(4-dimethylamino-3,5-diethylphenyl)phosphino]-1,1'-binaphthyl}ruthenium (II)

[Ru(OAc)$_2$(L)] L=(S)-2,2'-bis[bis(4-dimethylamino-3,5-diethylphenyl)phosphino]-1,1'-binaphthyl Under an argon atmosphere, to dichloro{(S)-2,2'-bis[bis(4-dimethylamino-3,5-diethylphenyl)phosphino]-1,1'-binaphthyl}ruthenium (II)-N,N-dimethylformamide complex (128.6 mg, 0.102 mmoL) synthesized in Example 24 was added a solution of sodium acetate (318.3 mg, 3.880 mmoL) in methanol (5 mL), and the mixture was ultrasonicated to allow reaction for 20 min. Toluene (5 mL) and water (5 mL) were added to the reaction mixture, and the mixture was partitioned. Toluene (5 mL) was added to the aqueous layer, and the mixture was partitioned. Water (5 mL) was added to all organic layers, and the mixture was partitioned. The solvent of the organic layer was evaporated to give the title compound (116.2 mg, brown powder).
$^{31}$P-NMR (121 MHz, $CD_2Cl_2$, 85% $H_3PO_4$) δ: 63.9 (s).

Example 26

Synthesis of dichloro{(S)-2,2'-bis[bis(4-dimethylamino-3,5-diisopropylphenyl)phosphino]-1,1'-binaphthyl}ruthenium (II)-N,N-dimethylformamide complex

[RuCl$_2$(L)(dmf)$_n$] L=(S)-2,2'-bis[bis(4-dimethylamino-3,5-diisopropylphenyl)phosphino]-1,1'-binaphthyl Under an argon atmosphere, to di-μ-chlorobis[(η$^6$-benzene)chlororuthenium (II)] (66.5 mg, 0.1330 mmoL) and (S)-2,2'-bis[bis(4-dimethylamino-3,5-diisopropylphenyl)phosphino]-1,1'-binaphthyl (300.5 mg, 0.2656 mmoL) synthesized in Example 9 was added N,N-dimethylformamide (6 mL), and the mixture was stirred at 120° C. for 3 hr. Then, the solvent was evaporated under reduced pressure to give the title compound (0.3792 g).
$^{31}$P-NMR (121 MHz, $CD_2Cl_2$, 85% $H_3PO_4$) δ: 34.5(s), 44.0(s).

Example 27

Synthesis of diacetato{(S)-2,2'-bis[bis(4-dimethylamino-3,5-diisopropylphenyl)phosphino]-1,1'-binaphthyl}ruthenium (II)

[Ru(OAc)$_2$(L)] L=(S)-2,2'-bis[bis(4-dimethylamino-3,5-diisopropylphenyl)phosphino]-1,1'-binaphthyl Under an argon atmosphere, to dichloro{(S)-2,2'-bis[bis(4-dimethylamino-3,5-diisopropylphenyl)phosphino]-1,1'-binaphthyl}ruthenium (II)-N,N-dimethylformamide complex (146.5 mg, 0.1046 mmoL) synthesized in Example 26 was added a solution of sodium acetate (322.6 mg, 3.933 mmoL) in methanol (5 mL), and the mixture was ultrasonicated to allow reaction for 20 min. Toluene (5 mL) and water (5 mL) were added to the reaction mixture, and the mixture was partitioned. Toluene (5 mL) was added to the aqueous layer, and the mixture was partitioned. Water (5 mL) was added to all organic layers, and the mixture was partitioned. The solvent of the organic layer was evaporated to give the title compound (152.3 mg, brown powder).
$^{31}$P-NMR (121 MHz, $CD_2Cl_2$, 85% $H_3PO_4$) δ: 65.5 (s).

Example 28

Synthesis of dichloro{(S)-2,2'-bis[bis(4-diethylaminophenyl)phosphino]-1,1'-binaphthyl}ruthenium (II)-N,N-dimethylformamide complex

[RuCl$_2$(L)(dmf)$_n$] L=(S)-2,2'-bis[bis(4-diethylaminophenyl)phosphino]-1,1'-binaphthyl Under an argon atmosphere, to di-μ-chlorobis[(η$^6$-benzene)chlororuthenium (II)] (26.6 mg, 0.0532 mmoL) and (S)-2,2'-bis[bis(4-diethylaminophenyl)phosphino]-1,1'-binaphthyl (97.7 mg, 0.1077 mmoL) synthesized in Example 12 was added N,N-dimethylformamide (6 mL), and the mixture was stirred at 120° C. for 2 hr. Then, the solvent was evaporated under reduced pressure to give the title compound (0.140 g).
$^{31}$P-NMR (121 MHz, $CD_2Cl_2$, 85% $H_3PO_4$) δ: 51.2(s).

Example 29

Synthesis of dichloro{(S)-2,2'-bis[bis[4-(pyrrolidin-1-yl)phenyl]phosphino]-1,1'-binaphthyl}ruthenium (II)-N,N-dimethylformamide complex

[RuCl$_2$(L)(dmf)$_n$] L=(S)-2,2'-bis[bis[4-(pyrrolidin-1-yl)phenyl]phosphino]-1,1'-binaphthyl Under an argon atmosphere, to di-μ-chlorobis[(η$^6$-benzene)chlororuthenium (II)] (27.0 mg, 0.054 mmoL) and (S)-2,2'-bis[bis[4-(pyrrolidin-1-yl)phenyl]phosphino]-1,1'-binaphthyl (97.3 mg, 0.1082 mmoL) synthesized in Example 15 was added N,N-dimethylformamide (5 mL), and the mixture was stirred at 120° C. for 2 hr. Then, the solvent was evaporated under reduced pressure to give the title compound (145 mg).
$^{31}$P-NMR (121 MHz, $CD_2Cl_2$, 85% $H_3PO_4$) δ: 52.6 (s).

Example 30

Synthesis of {(S)-2,2'-bis[bis(4-dimethylaminophenyl)phosphino]-1,1'-binaphthyl}bis(η$^3$-2-methylallyl)ruthenium (II)

[Ru(2-methylallyl)$_2$(L)] L=(S)-2,2'-bis[bis(4-dimethylaminophenyl)phosphino]-1,1'-binaphthyl Under an argon atmosphere, to (η$^2$,η$^2$-1,5-cyclooctadiene)bis(η$^3$-2-methylallyl)ruthenium (II) (19.4 mg, 0.0607 mmoL) and (S)-2,2'-bis[bis(4-dimethylaminophenyl)phosphino]-1,1'-binaphthyl (55.0 mg, 0.0692 mmoL) synthesized in Reference Example 8 was added toluene (2 mL), and the mixture was stirred at 110° C. for 14 hr. After cooling to room temperature, the mixture was filtrated, and the filtrate was evaporated under reduced pressure to give the title compound (68 mg, brown powder).
$^{31}$P-NMR (121 MHz, $CD_2Cl_2$, 85% $H_3PO_4$) δ: 38.2 (s).

Example 31

Synthesis of (η⁶-benzene)chloro{(S)-2,2'-bis[bis(4-dimethylaminophenyl)phosphino]-1,1'-binaphthyl}ruthenium (II) chloride

[RuCl(benzene)(L)]Cl L=(S)-2,2'-bis[bis(4-dimethylaminophenyl)phosphino]-1,1'-binaphthyl Under an argon atmosphere, to di-μ-chlorobis[(η⁶-benzene)chlororuthenium (II)] (50.9 mg, 0.102 mmoL) and (S)-2,2'-bis[bis(4-dimethylaminophenyl)phosphino]-1,1'-binaphthyl (161.4 mg, 0.203 mmoL) synthesized in Reference Example 8 were added ethanol (5 mL) and methylene chloride (5 mL), and the mixture was stirred at 50° C. for 1 hr. After the mixture was cooled to room temperature, the mixture was filtrated, and the filtrate was evaporated under reduced pressure to give the title compound (225.4 mg, brown powder).
³¹P-NMR (121 MHz, $CD_2Cl_2$, 85% $H_3PO_4$) δ: 26.0(d, J=63.3 Hz), 33.1 (d, J=62.7 Hz).

Example 32

Synthesis of diethylammonium {tri-1-chlorobis[chloro[(S)-2,2'-bis[bis(4-dimethylaminophenyl)phosphino]-1,1'-binaphthyl]ruthenate(II)]}

($NH_2Et_2$)[{RuCl(L)}₂(μ-Cl)₃] L=(S)-2,2'-bis[bis(4-dimethylaminophenyl)phosphino]-1,1'-binaphthyl Under an argon atmosphere, to (η⁶-benzene)chloro {(S)-2,2'-bis[bis(4-dimethyl aminophenyl)phosphino]-1,1'-binaphthyl }ruthenium (II) chloride (100.6 mg, 0.097 mmoL) synthesized in Example 31 and diethylamine hydrochloride (11.6 mg, 0.106 mmoL) was added tetrahydrofuran (20 mL), and the mixture was stirred at 80° C. for 20 hr. After the mixture was cooled to room temperature, the mixture was filtrated, and the filtrate was evaporated under reduced pressure to give the title compound (150.8 mg, brown powder).
³¹P-NMR (121 MHz, $CD_2Cl_2$, 85% $H_3PO_4$) δ: 47.3(d, J=37.5 Hz) 52.4 (d, J=38.8 Hz).

Example 33

Synthesis of dichloro{(S)-2,2'-bis[bis(4-dimethylaminophenyl)phosphino]-1,1'-binaphthyl}[(1S,2S)-(−)-1,2-diphenylethylenediamine]ruthenium (II)

[RuCl₂(L)(X)] L=(S)-2,2'-bis[bis(4-dimethylaminophenyl)phosphino]-1,1'-binaphthyl, X=(1S,2S)-(−)-1,2-diphenylethylenediamine Under an argon atmosphere, to di-μ-chlorobis[(η⁶-benzene)chlororuthenium (II)] (21.2 mg, 0.042 mmoL) and (S)-2,2'-bis[bis(4-dimethylaminophenyl)phosphino]-1,1'-binaphthyl (70.3 mg, 0.088 mmoL) synthesized in Reference Example 8 was added N,N-dimethylformamide (2 mL), and the mixture was stirred at 120° C. for 1 hr. Then, the solvent was evaporated under reduced pressure. A solution of (1S,2S)-(−)-1,2-diphenylethylenediamine (18.8 mg, 0.089 mmoL) in 2-propanol (5 mL) was added to the obtained compound, and the mixture was stirred at room temperature for 90 min to give the title compound (53.1 mg, ocher powder).
³¹P-NMR (121 MHz, $CD_2Cl_2$, 85% $H_3PO_4$) δ: 42.6(s).

Example 34

Synthesis of dichloro{(S)-2,2'-bis[bis(4-dimethylamino-3,5-dimethylphenyl)phosphino]-1,1'-binaphthyl}[(1S,2S)-(−)-1,2-diphenylethylenediamine]ruthenium (II)

[RuCl₂(L)(X)] L=(S)-2,2'-bis[bis(4-dimethylamino-3,5-dimethylphenyl)phosphino]-1,1'-binaphthyl, X=(1S,2S)-(−)-1,2-diphenylethylenediamine Under an argon atmosphere, to di-μ-chlorobis[(η⁶-benzene)chlororuthenium (II)] (50.4 mg, 0.101 mmoL) and (S)-2,2'-bis[bis(4-dimethylamino-3,5-dimethylphenyl)phosphino]-1,1'-binaphthyl (191.1 mg, 0.211 mmoL) synthesized in Example 3 was added N,N-dimethylformamide (3 mL), and the mixture was stirred at 120° C. for 1 hr. Then, the solvent was evaporated under reduced pressure. A solution of (1S,2S)-(−)-1,2-diphenylethylenediamine (44.4 mg, 0.209 mmoL) in 2-propanol (7 mL) was added to the obtained compound, and the mixture was stirred at room temperature for 6 hr to give the title compound (276.7 mg, ocher powder).
³¹P-NMR (121 MHz, $CD_2Cl_2$, 85% $H_3PO_4$) δ: 42.6(s).

Example 35

Synthesis of dichloro{(S)-2,2'-bis[bis(4-dimethylamino-3,5-diethylphenyl)phosphino]-1,1'-binaphthyl}[(1S,2S)-(−)-1,2-diphenylethylenediamine]ruthenium (II)

[RuCl₂(L)(X)]L=(S)-2,2'-bis[bis(4-dimethylamino-3,5-diethylphenyl)phosphino]-1,1'-binaphthyl, X=(1S,2S)-(−)-1,2-diphenylethylenediamine Under an argon atmosphere, to di-μ-chlorobis[(η⁶-benzene)chlororuthenium (II)] (13.8 mg, 0.028 mmoL) and (S)-2,2'-bis[bis(4-dimethylamino-3,5-diethylphenyl)phosphino]-1,1'-binaphthyl (57.9 mg, 0.057 mmoL) synthesized in Example 6 was added N,N-dimethylformamide (2 mL), and the mixture was stirred at 120° C. for 1 hr. Then, the solvent was evaporated under reduced pressure. A solution of (1S,2S)-(−)-1,2-diphenylethylenediamine (6.1 mg, 0.029 mmoL) in 2-propanol (5 mL) was added to the obtained compound, and the mixture was stirred at room temperature for 90 min to give the title compound (75.9 mg, ocher powder).
³¹P-NMR (121 MHz, $CD_2Cl_2$, 85% $H_3PO_4$) δ: 45.0(s).

Example 36

Synthesis of dichloro{(S)-2,2'-bis[bis(4-dimethylamino-3,5-diisopropylphenyl)phosphino]-1,1'-binaphthyl}[(1S,2S)-(−)-1,2-diphenylethylenediamine] ruthenium (II)

[RuCl₂(L)(X)]L(S)-2,2'-bis[bis(4-dimethylamino-3,5-diisopropylphenyl)phosphino]-1,1'-binaphthyl, X=(1S,2S)-(−)-1,2-diphenylethylenediamine Under an argon atmosphere, to di-μ-chlorobis[(η⁶-benzene) chlororuthenium (II)] (19.8 mg, 0.040 mmoL) and (S)-2,2'-bis[bis(4-dimethylamino-3,5-diisopropylphenyl)phosphino]-1,1'-binaphthyl (90.8 mg, 0.080 mmoL) synthesized in Example 9 was added N,N-dimethylformamide (2 mL), and the mixture was stirred at 120° C. for 1 hr. Then, the solvent was evaporated under reduced pressure. A solution of (1S,2S)-(−)-1,2-diphenylethylenediamine (19.0 mg, 0.090 mmoL) in 2-propanol (5 mL) was added to the obtained compound, and the mixture was stirred at room temperature for 90 min to give the title compound (115.4 mg, ocher powder).

$^{31}$P-NMR (121 MHz, CD$_2$Cl$_2$, 85% H$_3$PO$_4$) δ: 47.7(s).

Example 37

Synthesis of (η$^2$, η$^2$-1,5-cyclooctadiene){(S)-2,2'-bis[bis(4-dimethylaminophenyl)phosphino]-1,1'-binaphthyl}rhodium (I) perchlorate

[Rh(cod)(L)]ClO$_4$ L=(S)-2,2'-bis[bis(4-dimethylaminophenyl)phosphino]-1,1'-binaphthyl Under an argon atmosphere, to di-μ-chlorobis[(η$^2$,η$^2$-1,5-cyclooctadiene)rhodium (I)] (48.0 mg, 0.0973 mmoL) and silver perchlorate (43.4 mg, 0.209 mmoL) was added acetone (7.5 mL), and the mixture was stirred at room temperature for 1 hr. The insoluble material was removed by filtration and the filtrate was added to (S)-2,2'-bis[bis(4-dimethylaminophenyl)phosphino]-1,1'-binaphthyl (156.1 mg, 0.196 mmoL) synthesized in Reference Example 8. The mixture was stirred at room temperature for 1 hr. After the insoluble material was removed by filtration, the solvent was evaporated under reduced pressure to give the title compound (0.2312 g).

$^1$H-NMR (300 MHz, CD$_2$Cl$_2$, CD$_2$Cl$_2$) δ: 2.8(s, 12H), 3.1(s, 12H), 4.6(m, 2H), 4.9(m, 2H), 5.9(d, 4H, J=7.6 Hz), 6.5(d, 2H, J=8.5 Hz), 6.8(d, 4H, J=8.6 Hz), 6.9(m, 2H), 7.1 (m, 4H), 7.3-7.5(m, 6H), 7.6-7.7(m, 4H), 7.8-7.9(m, 2H).

$^{31}$P-NMR (121 MHz, CD$_2$Cl$_2$, 85% H$_3$PO$_4$) δ: 21.6(s), 22.8(s).

Example 38

Synthesis of (η$^2$,η$^2$-1,5-cyclooctadiene){(S)-2,2'-bis[bis(4-dimethylamino-3,5-dimethylphenyl)phosphino]-1,1'-binaphthyl}rhodium (I) perchlorate

[Rh(cod)(L)]ClO$_4$ L=(S)-2,2'-bis[bis(4-dimethylamino-3,5-dimethylphenyl)phosphino]-1,1'-binaphthyl Under an argon atmosphere, to di-μ-chlorobis[(η$^2$,η$^2$-1,5-cyclooctadiene)rhodium (I)] (101.6 mg, 0.206 mmoL) and silver perchlorate (86.7 mg, 0.418 mmoL) was added acetone (20 mL), and the mixture was stirred at room temperature for 1 hr. The insoluble material was removed by filtration and the filtrate was added to (S)-2,2'-bis[bis(4-dimethylamino-3,5-dimethylphenyl)phosphino]-1,1'-binaphthyl (375.1 mg, 0.413 mmoL) synthesized in Example 3. The mixture was stirred at room temperature for 1 hr. After the insoluble material was removed by filtration, the solvent was evaporated under reduced pressure to give the title compound (0.5427 g).

$^1$H-NMR (300 MHz, CD$_2$Cl$_2$, CD$_2$Cl$_2$) δ: 1.9(s, 12H), 2.3(s, 12H), 2.2-2.5(m, 8H), 2.6(s, 12H), 2.9(s, 12H), 4.61 (mb, 2H), 4.9(mb, 2H), 6.5(d, 2H, J=8.6 Hz), 6.9-7.0(m, 4H), 7.0-7.1(m, 2H), 7.1-7.2(m, 4H), 7.3-7.4(m, 2H), 7.7-7.9(m, 6H).

$^{31}$P-NMR (121 MHz, CD$_2$Cl$_2$, 85% H$_3$PO$_4$) δ: 22.9(s), 24.1(s).

Example 39

Synthesis of (η$^2$,η$^2$-1,5-cyclooctadiene){(S)-2,2'-bis[bis(4-dimethylamino-3,5-diethylphenyl)phosphino]-1,1'-binaphthyl}rhodium (I) perchlorate

[Rh(cod)(L)]ClO$_4$ L=(S)-2,2'-bis[bis(4-dimethylamino-3,5-diethylphenyl)phosphino]-1,1'-binaphthyl Under an argon atmosphere, to di-μ-chlorobis[(η$^2$,η$^2$-1,5-cyclooctadiene)rhodium (I)] (47.2 mg, 0.0957 mmoL) and silver perchlorate (40.0 mg, 0.193 mmoL) was added acetone (10 mL), and the mixture was stirred at room temperature for 1 hr. The insoluble material was removed by filtration and the filtrate was added to (S)-2,2'-bis[bis(4-dimethylamino-3,5-diethylphenyl)phosphino]-1,1'-binaphthyl (198.8 mg, 0.195 mmoL) synthesized in Example 6. The mixture was stirred at room temperature for 1 hr. After the insoluble material was removed by filtration, the solvent was evaporated under reduced pressure to give the title compound (0.27 g).

$^{31}$P-NMR (121 MHz, CD$_2$Cl$_2$, 85% H$_3$PO$_4$) δ: 25.2(s), 26.4(s).

Example 40

Synthesis of (η$^2$,η$^2$-1,5-cyclooctadiene){(S)-2,2'-bis[bis(4-dimethylamino-3,5-diisopropylphenyl)phosphino]-1,1'-binaphthyl}rhodium (I) perchlorate

[Ru(cod)(L)]ClO$_4$ L=(S)-2,2'-bis[bis(4-dimethylamino-3,5-diisopropylphenyl)phosphino]-1,1'-binaphthyl Under an argon atmosphere, to di-μ-chlorobis[(η$^2$,η$^2$-1,5-cyclooctadiene)rhodium (I)] (25.2 mg, 0.0511 mmoL) and silver perchlorate (21.3 mg, 0.103 mmoL) was added acetone (5 mL), and the mixture was stirred at room temperature for 1 hr. The insoluble material was removed by filtration and the filtrate was added to (S)-2,2'-bis[bis(4-dimethylamino-3,5-diisopropylphenyl)phosphino]-1,1'-binaphthyl (122.2 mg, 0.108 mmoL) synthesized in Example 9. The mixture was stirred at room temperature for 1 hr. After the insoluble material was removed by filtration, the solvent was evaporated under reduced pressure to give the title compound (0.151 g).

$^{31}$P-NMR (121 MHz, CD$_2$Cl$_2$, 85% H$_3$PO$_4$) δ: 26.2(s), 27.4(s).

Example 41

Synthesis of (η$^2$,η$^2$-1,5-cyclooctadiene){(S)-2,2'-bis[bis(4-dimethylamino-3,5-dimethylphenyl)phosphino]-1,1'-binaphthyl}rhodium (I) trifluoromethanesulfonate

[Rh(cod)(L)]OTf L=(S)-2,2'-bis[bis(4-dimethylamino-3,5-dimethylphenyl)phosphino]-1,1'-binaphthyl Under an argon atmosphere, to bis(η$^2$,η$^2$-1,5-cyclooctadiene)rhodium (I) trifluoromethanesulfonate (49.3 mg, 0.1053 mmoL) and (S)-2,2'-bis[bis(4-dimethylamino-3,5-dimethylphenyl)phosphino]-1,1'-binaphthyl (95.5 mg, 0.1053 mmoL) synthesized in Example 3 was added tetrahydrofuran (10 mL), and the mixture was stirred at 40° C. for 1 hr. The solvent was evaporated under reduced pressure to give the title compound (134 mg).

$^{31}$P-NMR (121 MHz, CD$_2$Cl$_2$, 85% H$_3$PO$_4$) δ: 22.9(s), 24.1(s).

Example 42

Synthesis of (π-allyl){(S)-2,2'-bis[bis(4-dimethylamino-3,5-dimethylphenyl)phosphino]-1,1'-binaphthyl}palladium (II) perchlorate

[Pd(π-allyl)(L)]ClO$_4$ L=(S)-2,2'-bis[bis(4-dimethylamino-3,5-dimethylphenyl)phosphino]-1,1'-binaphthyl Under an argon atmosphere, to di-μ-chlorobis[(π-allyl)palladium (II)] (13.15 mg, 0.05 mmol) and (S)-2,2'-bis[bis(4-dimethylamino-3,5-dimethylphenyl)phosphino]-1,1'-binaphthyl (90.7 mg, 0.1 mmol) synthesized in Example 3 was added methanol (2 mL), and the mixture was stirred at room temperature for 20 min. Methanol (2 mL) was added to the mixture, and the mixture was stirred at room temperature for 50 min. The operation was repeated twice. A solution of lithium perchlorate trihydrate (16 mg, 0.1 mmol) in methanol (2 mL) was added thereto, and the mixture was stirred at room temperature for 1 hr. Water (12 mL) was added to the mixture to give the title compound (87 mg). yield 75.2%.

$^1$H-NMR (300 MHz, CDCl$_3$) δ: 1.81 (d, J=8.0 Hz, 12 H), 2.34 (d, J=5.8 Hz, 12 H), 2.56 (d, J=4.1 Hz, 12 H), 2.87 (d, J=3.7 Hz, 12 H), 2.94-3.02 (m, 1 H), 3.93-4.25 (m, 3 H), 5.67-5.79 (m, 1 H), 6.42 (d, J=8.5 Hz, 1 H), 6.50 (d, J=12.7 Hz, 2 H), 6.61 (d, J=8.7 Hz, 1 H), 6.76 (d, J=12.9 Hz, 2 H), 6.98-7.11 (m, 2 H), 7.25-7.42 (m, 8 H), 7.60-7.67 (m, 4 H).

$^{13}$C-NMR (75 MHz, CDCl$_3$) δ: 19.1, 19.7, 42.2, 42.4, 126.0, 126.2, 126.5, 126.6, 126.9, 127.1, 127.3, 127.6, 127.8, 128.2, 133.4, 133.7, 133.9, 134.1, 135.1, 135.4, 135.6, 135.8, 136.0, 137.0, 137.1, 137.2, 152.3

$^{31}$P-NMR (121.5 MHz, CDCl$_3$) δ: 20.0 (d, J=49.3 Hz), 22.6 (d, J=49.1 Hz).

MS (FAB), m/z=1053 (M$^+$).

Example 43

Synthesis of dichloro{(S)-2,2'-bis[bis(4-dimethylamino-3,5-dimethylphenyl)phosphino]-1,1'-binaphthyl}palladium (II)

[PdCl$_2$(L)]L=(S)-2,2'-bis[bis(4-dimethylamino-3,5-dimethylphenyl)phosphino]-1,1'-binaphthyl Under an argon atmosphere, to a solution of dichlorobis(acetonitrile)palladium (II) (104 mg, 0.40 mmol) in benzene (4 mL) was added a solution of (S)-2,2'-bis[bis(4-dimethylamino-3,5-dimethylphenyl)phosphino]-1,1'-binaphthyl (363 mg, 0.40 mmol) synthesized in Example 3 in benzene (4 mL), and the mixture was stirred at room temperature for 17 hr. The solvent was evaporated to give the title compound (440 mg).

$^1$H-NMR (300 MHz, CDCl$_3$) δ: 1.83 (s, 12 H), 2.29 (s, 12 H), 2.57 (s, 12 H), 2.82 (s, 12 H), 6.59 (d, J=8.5 Hz, 2 H), 7.04-7.50 (m, 14 H), 7.58-7.63 (m, 4 H).

$^{31}$P-NMR (121.5 MHz, CDCl$_3$) δ 28.5 (s).

MS (FAB), m/z=1081 (M–H$^+$), m/z=1047 (M–Cl$^+$).

Example 44

Synthesis of {di-μ-hydroxobis[[(S)-2,2'-bis[bis(4-dimethylamino-3,5-dimethylphenyl)phosphino]-1,1'-binaphthyl]palladium (II)]}bistetrafluoroborate

[{Pd(L)}$_2$(μ-OH)$_2$](BF$_4$)$_2$ L=(S)-2,2'-bis[bis(4-dimethylamino-3,5-dimethylphenyl)phosphino]-1,1'-binaphthyl Under an argon atmosphere, dichloro{(S)-2,2'-bis[bis(4-dimethylamino-3,5-dimethylphenyl)phosphino]-1,1'-binaphthyl}palladium (II) (108.4 mg, 0.10 mmol) synthesized in Example 43 was stirred with dichloromethane (10.8 mL), water (1 mL), silver tetrafluoroborate (38.9 mg, 0.20 mmol) and molecular sieves 4A (1.5 g) at room temperature for 29 hr, and the insoluble material was removed by filtration. The solvent of the filtrate was evaporated to give the title compound (67 mg). yield 60.0%.

$^1$H-NMR (300 MHz, CDCl$_3$) δ: −2.88 (s, 2 H), 1.98 (br s, 24 H), 2.08 (s, 24 H), 2.45 (s, 24 H), 2.63 (s, 24 H), 6.26 (d, J=8.6 Hz, 4 H), 6.98-7.12 (m, 20 H), 7.28-7.39 (m, 8 H), 7.73 (d, J=8.2 Hz, 4 H), 7.83 (d, J=8.7 Hz, 4 H).

$^{31}$P-NMR (121.5 MHz, CDCl$_3$) δ: 28.4 (s).

Example 45

Synthesis of (η$^2$,η$^2$-1,5-cyclooctadiene){(S)-2,2'-bis[bis(4-dimethylaminophenyl)phosphino]-1,1'-binaphthyl}iridium (I) tetrafluoroborate

[Ir(cod)(L)]BF$_4$ L=(S)-2,2'-bis[bis(4-dimethylaminophenyl)phosphino]-1,1'-binaphthyl Under an argon atmosphere, to bis(η$^2$,η$^2$-1,5-cyclooctadiene)iridium (I) tetrafluoroborate (9.9 mg, 0.020 mmoL) and (S)-2,2'-bis[bis(4-dimethylaminophenyl)phosphino]-1,1'-binaphthyl (15.7 mg, 0.020 mmoL) synthesized in Reference Example 8 was added dichloromethane (1 mL), and the mixture was stirred at room temperature to give the title compound.

$^{31}$P-NMR (121 MHz, CD$_2$Cl$_2$, 85% H$_3$PO$_4$) δ: 12.8(s).

Example 46

Synthesis of (η$^2$,η$^2$-1,5-cyclooctadiene){(S)-2,2'-bis[bis(4-dimethylamino-3,5-dimethylphenyl)phosphino]-1,1'-binaphthyl}iridium (I) tetrafluoroborate

[Ir(cod)(L)]BF$_4$ L=(S)-2,2'-bis[bis(4-dimethylamino-3,5-dimethylphenyl)phosphino]-1,1'-binaphthyl Under an argon atmosphere, to bis(η$^2$,η$^2$-1,5-cyclooctadiene)iridium (I) tetrafluoroborate (10.9 mg, 0.022 mmoL) and (S)-2,2'-bis[bis(4-dimethylamino-3,5-dimethylphenyl)phosphino]-1,1'-binaphthyl (20.1 mg, 0.022 mmoL) synthesized in Example 3 was added dichloromethane (1 mL), and the mixture was stirred at room temperature to give the title compound.

$^{31}$P-NMR (121 MHz, CD$_2$Cl$_2$, 85% H$_3$PO$_4$) δ: 14.1(s).

Example 47

Synthesis of (η²,η²-1,5-cyclooctadiene){(S)-2,2'-bis[bis(4-dimethylamino-3,5-diethylphenyl)phosphino]-1,1'-binaphthyl}iridium (I) tetrafluoroborate

[Ir(cod)(L)]BF₄ L=(S)-2,2'-bis[bis(4-dimethylamino-3,5-diethylphenyl)phosphino]-1,1'-binaphthyl Under an argon atmosphere, to bis(η²,η²-1,5-cyclooctadiene)iridium (I) tetrafluoroborate (10.7 mg, 0.022 mmoL) and (S)-2,2'-bis[bis(4-dimethylamino-3,5-diethylphenyl)phosphino]-1,1'-binaphthyl (22.0 mg, 0.022 mmoL) synthesized in Example 6 was added dichloromethane (1 mL), and the mixture was stirred at room temperature to give the title compound.

$^{31}$P-NMR (121 MHz, CD₂Cl₂, 85% H₃PO₄) δ: 15.4(s).

Example 48

Synthesis of (η²,η²-1,5-cyclooctadiene){(S)-2,2'-bis[bis(4-diethylaminophenyl)phosphino]-1,1'-binaphthyl}iridium (I) tetrafluoroborate

[Ir(cod)(L)]BF₄ L=(S)-2,2'-bis[bis(4-diethylaminophenyl)phosphino]-1,1'-binaphthyl Under an argon atmosphere, to bis(η²,η²-1,5-cyclooctadiene)iridium (I) tetrafluoroborate (9.5 mg, 0.019 mmoL) and (S)-2,2'-bis[bis(4-diethylaminophenyl)phosphino]-1,1'-binaphthyl (17.4 mg, 0.019 mmoL) synthesized in Example 12 was added dichloromethane (1 mL), and the mixture was stirred at room temperature to give the title compound.

$^{31}$P-NMR (121 MHz, CD₂Cl₂, 85% H₃PO₄) δ: 12.5(s).

Example 49

Synthesis of (η²,η²-1,5-cyclooctadiene){(S)-2,2'-bis[bis[4-(pyrrolidin-1-yl)phenyl]phosphino]-1,1'-binaphthyl}iridium (I) tetrafluoroborate

[Ir(cod)(L)]BF₄ L=(S)-2,2'-bis[bis[4-(pyrrolidin-1-yl)phenyl]phosphino]-1,1'-binaphthyl Under an argon atmosphere, to bis(η²,η²-1,5-cyclooctadiene)iridium (I) tetrafluoroborate (5.2 mg, 0.011 mmoL) and (S)-2,2'-bis[bis[4-(pyrrolidin-1-yl)phenyl]phosphino]-1,1'-binaphthyl (13.3 mg, 0.011 mmoL) synthesized in Example 15 was added dichloromethane (1 mL), and the mixture was stirred at room temperature to give the title compound.

$^{31}$P-NMR (121 MHz, CD₂Cl₂, 85% H₃PO₄) δ: 13.1(s).

Example 50

Synthesis of {(S)-2,2'-bis[bis(4-dimethylamino-3,5-dimethylphenyl)phosphino]-1,1'-binaphthyl}bis(acetonitrile)copper(I) perchlorate

[Cu(L)(CH₃CN)₂]ClO₄ L=(S)-2,2'-bis[bis(4-dimethylamino-3,5-dimethylphenyl)phosphino]-1,1'-binaphthyl Under an argon atmosphere, tetrakis(acetonitrile)copper(I) perchlorate (163 mg, 0.50 mmol), (S)-2,2'-bis[bis(4-dimethylamino-3,5-dimethylphenyl)phosphino]-1,1'-binaphthyl (454 mg, 0.50 mmol) synthesized in Example 3 and dichloromethane (25 mL) were added, and the mixture was stirred at room temperature for 40 min. After concentration under reduced pressure at 25° C., the concentrate was dried in vacuo at room temperature to give the title compound (565 mg) (yellow crystals, yield 98.1%).

$^{1}$H-NMR (300 MHz, CDCl₃) δ: 1.76 (s, 12 H), 2.29 (s, 6 H), 2.35 (s, 12 H), 2.52 (s, 12 H), 2.86 (s, 12 H), 6.59-6.63 (m, 6 H), 6.99-7.04 (m, 2 H), 7.16-7.32 (m, 4 H), 7.46-7.61 (m, 8 H).

$^{31}$P-NMR (121.5 MHz, CDCl₃) δ: −2.04 (s).

Example 51

Synthesis of {(S)-2,2'-bis[bis(4-dimethylaminophenyl)phosphino]-1,1'-binaphthyl}bis(acetonitrile)copper(I) perchlorate

[Cu(L)(CH₃CN)₂]ClO₄ L=(S)-2,2'-bis[bis(4-dimethylaminophenyl)phosphino]-1,1'-binaphthyl Under an argon atmosphere, tetrakis(acetonitrile)copper(I) perchlorate (163 mg, 0.50 mmol), (S)-2,2'-bis[bis(4-dimethylaminophenyl)phosphino]-1,1'-binaphthyl (397 mg, 0.50 mmol) synthesized in Reference Example 8 and dichloromethane (25 mL) were added, and the mixture was stirred at room temperature for 30 min. After concentration under reduced pressure at 25° C., the concentrate was dried in vacuo to give the title compound (523 mg) (yellow crystals, yield 100.5%).

$^{31}$P-NMR (121.5 MHz, CDCl₃) δ: −3.0 (s).

Example 52

Synthesis of dichloro{(S)-2,2'-bis[bis(4-dimethylaminophenyl)phosphino]-1,1'-binaphthyl}palladium (II)

[PdCl₂(L)] L=(S)-2,2'-bis[bis(4-dimethylaminophenyl)phosphino]-1,1'-binaphthyl

Under an argon atmosphere, dichlorobis(acetonitrile)palladium (II) (52 mg, 0.20 mmol), (S)-2,2'-bis[bis(4-dimethylaminophenyl)phosphino]-1,1'-binaphthyl (159 mg, 0.20 mmol) synthesized in Reference Example 8 and benzene (24 mL) were added, and the mixture was stirred at room temperature for 24 hr. The insoluble material was removed by filtration, the filtrate was concentrated under reduced pressure at 25° C., and the concentrate was dried in vacuo to give the title compound (115 mg) (orange crystals, yield 59.1%).

$^{1}$H-NMR (300 MHz, CDCl₃) δ: 2.7 (s, 12 H), 3.0 (s, 12 H), 5.9 (d, J=7.8 Hz, 4 H), 6.7 (d, J=7.5 Hz, 4 H), 6.8 (d, J=8.6 Hz, 2 H), 7.1 (t, J=7.4 Hz, 2 H), 7.3-7.5 (m, 10 H), 7.6 (d, J=8.1 Hz, 2 H), 7.6-7.7 (m, 4 H).

$^{31}$P-NMR (121.5 MHz, CDCl₃) δ: 27.4 (s).

MS (FAB) m/z=969 (M−H⁺), m/z=935 (M−Cl⁺).

Example 53

Asymmetric hydrogenation of 2-amino-5-chloro-2', 3'-dimethoxybenzophenone

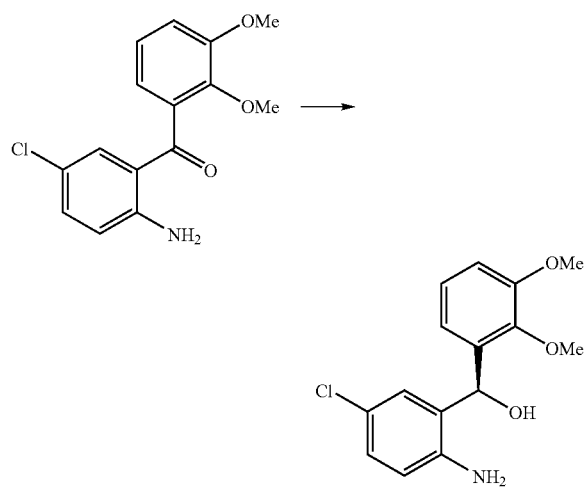

Under an argon atmosphere, to dichloro(η²,η²-1,5-cyclooctadiene)ruthenium (II) (119.7 mg, 0.43 mmol) and (S)-2,2'-bis[bis(4-dimethylamino-3,5-dimethylphenyl)phosphino]-1,1'-binaphthyl (429.8 mg, 0.47 mmol) synthesized in Example 3 were added toluene (7.5 mL) and triethylamine (0.35 mL), and the mixture was stirred with heating at 135° C. for 3 hr. The solvent was evaporated under reduced pressure. To the residue (24.3 mg, 10.71 μmol) and (1S,2S)-(−)-1,2-diphenylethylenediamine ((S,S)-DPEN) (49.0 mg, 68.8 μmol) was added a mixture (15 mL) of 2-propanol/tetrahydrofuran (14/11), and the mixture was stirred for 1 hr. The reaction mixture was poured into 2-amino-5-chloro-2',3'-dimethoxybenzophenone (6.25 g, 21.42 mmol) and potassium hydroxide (47.7 mg, 0.85 mmol), and the mixture was subjected to hydrogenation under a 1 MPa hydrogen pressure at 23° C. TOF (mmoL/μmoL·h, turnover frequency) was $29.0 \times 10^{-3}$. The reaction mixture was analyzed by HPLC (column: CHIRALCEL OJ-RH, 4.6 mm×15 cm) to find an optical purity of 96.0% ee(S).

Comparative Example 3

Asymmetric hydrogenation of 2-amino-5-chloro-2', 3'-dimethoxybenzophenone

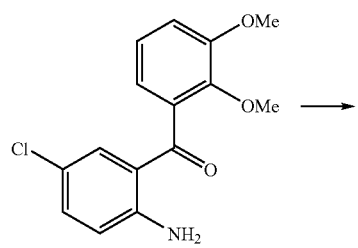

-continued

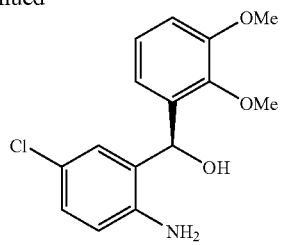

Under an argon atmosphere, to dichloro(η²,η²-1,5-cyclooctadiene)ruthenium (II) (149.6 mg, 0.53 mmol) and (S)-2,2'-bis[bis(3,5-dimethylphenyl)phosphino]-1,1'-binaphthyl (433.7 mg, 0.59 mmol) were added toluene (9 mL) and triethylamine (0.45 mL), and the mixture was stirred with heating at 135° C. for 3 hr. The solvent was evaporated under reduced pressure. To the residue (20.6 mg, 10.71 μmol) and (1S,2S)-(−)-1,2-diphenylethylenediamine ((S,S)-DPEN) (49.0 mg, 68.8 μmol) was added a mixture (15 mL) of 2-propanol/tetrahydrofuran (14/11), and the mixture was stirred for 1 hr. The reaction mixture was poured into 2-amino-5-chloro-2',3'-dimethoxybenzophenone (6.25 g, 21.42 mmol) and potassium hydroxide (47.7 mg, 0.85 mmol), and the mixture was subjected to hydrogenation under a 1 MPa hydrogen pressure at 23° C. TOF (mmoL/μmoL·h, turnover frequency) was $10.0 \times 10^{-3}$. The reaction mixture was analyzed by HPLC (column: CHIRALCEL OJ-RH, 4.6 mm×15 cm) to find an optical purity of 96.0% ee(S).

Example 54

Asymmetric hydrogenation of ethyl(Z)-3-acetylamino-3-phenyl-acrylate

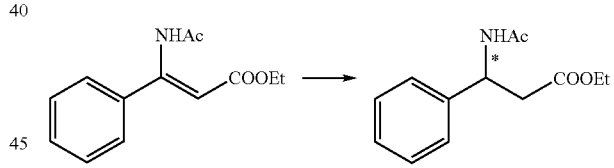

Under an argon atmosphere, to bis(η²,η²-1,5-cyclooctadiene)rhodium (I) trifluoromethanesulfonate (1.1 mg, 0.0023 mmol) and (S)-2,2'-bis[bis(4-diethylaminophenyl)phosphino]-1,1'-binaphthyl (3.0 mg, 0.0033 mmol) synthesized in Example 12 was added methanol (2 mL), and the mixture was stirred for 30 min. The solution was reacted with a solution of ethyl(Z)-3-acetylamino-3-phenyl-acrylate (37.4 mg, 0.160 mmol) in methanol (0.5 mL) under a 1 MPa hydrogen pressure at 25° C. for 15 hr. The obtained reaction mixture was analyzed by liquid chromatography (column: CHIRALCEL OJ-H) to find an optical purity of 50.9% ee(R). The conversion ratio was analyzed by ¹H-NMR and found to be 100%.

Examples 55-58

According to the method of Example 54, the reaction was carried out using the optically active ligands of Examples 3, 6 and 15, and Reference Example 8. The results are shown in Table 1.

TABLE 1

| Example | ligand | ee, % | Conv., % | absolute configuration |
|---|---|---|---|---|
| 55 | Example 3 | 72.8 | 100 | R |
| 56 | Reference Example 8 | 60.4 | 100 | R |
| 57 | Example 6 | 76.3 | 100 | R |
| 58 | Example 15 | 42.3 | 100 | R |

Comparative Example 4

Asymmetric hydrogenation of ethyl(Z)-3-acetylamino-3-phenyl-acrylate

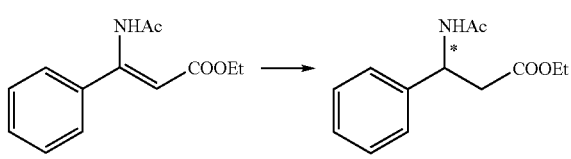 [SMILES: CCOC(=O)/C=C(/NC(C)=O)c1ccccc1 ; CCOC(=O)CC(NC(C)=O)c1ccccc1]

According to the method of Example 54, the reaction was carried out using (S)-2,2'-bis[diphenylphosphino]-1,1'-binaphthyl (BINAP) as a ligand. As a result, the optical purity was 36.9% ee(R). The conversion ratio was analyzed by $^1$H-NMR and found to be 100%.

Example 59

Asymmetric Hydrogenation of Itaconic Acid

Under an argon atmosphere, to bis($\eta^2$,$\eta^2$-1,5-cyclooctadiene)rhodium (I) trifluoromethanesulfonate (1.0 mg, 0.0021 mmol) and (S)-2,2'-bis[bis(4-dimethylaminophenyl)phosphino]-1,1'-binaphthyl (4.6 mg, 0.0058 mmol) synthesized in Reference Example 8 was added methanol (4 mL), and the mixture was stirred for 30 min. The reaction mixture was added to a solution of itaconic acid (21.8 mg, 0.168 mmol) in methanol (1 mL), and the mixture was subjected to hydrogenation under a 1 MPa hydrogen pressure at 25° C. for 15 hr. 2 mL of the reaction mixture was taken, sulfuric acid was added and the mixture was refluxed at 85° C. for 1 hr. The methylated solution was analyzed by gas chromatography (column: βDEX-225 (0.25 mm i.d.×30 m, 0.25 μm)) to find a conversion ratio of 100%, and an optical purity of 56.2% ee.

Examples 60-63

According to the method of Example 59, the reaction was carried out using the optically active ligands of Examples 3, 6, 12 and 15. The results are shown in Table 2.

TABLE 2

| Example | ligand | ee, % | Conv., % | absolute configuration |
|---|---|---|---|---|
| 60 | Example 3 | 61.9 | 100 | R |
| 61 | Example 6 | 29.9 | 100 | R |
| 62 | Example 12 | 64.1 | 100 | R |
| 63 | Example 15 | 47.3 | 100 | R |

Comparative Example 5

Asymmetric Hydrogenation of Itaconic Acid

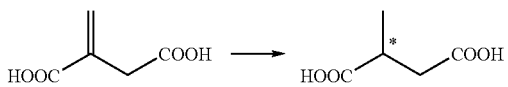

According to the method of Example 57, the reaction was carried out using (S)-2,2'-bis[diphenylphosphino]-1,1'-binaphthyl (BINAP) as a ligand. As a result, the conversion ratio was 100% and the optical purity was 6.9% ee(R).

Example 64

Asymmetric Isomerization of N,N-diethylnerylamine

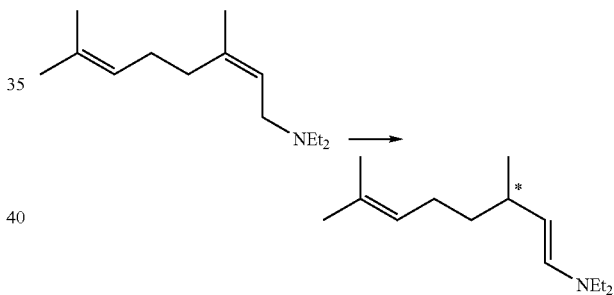

($\eta^2$,$\eta^2$-1,5-Cyclooctadiene){(S)-2,2'-bis[bis(4-dimethylamino-3,5-dimethylphenyl)phosphino]-1,1'-binaphthyl}rhodium (I) perchlorate (25.9 mg, 0.0213 mmoL) synthesized in Example 38 and N,N-diethylnerylamine (480 mg, 2.296 mmoL) were dissolved in tetrahydrofuran (5 mL), and the mixture was subjected to isomerization at 40° C. TOF (moL/moL·h, turnover frequency) was 131.9. The reaction mixture was analyzed by gas chromatography (column: Inert Cap CHIRAMIX, 0.32 mm×30 m) to find a conversion ratio of 100% and an optical purity of 100% ee(S).

Reference Example 9

Synthesis of ($\eta^2$,$\eta^2$-1,5-cyclooctadiene){(S)-2,2'-bis[diphenylphosphino]-1,1'-binaphthyl}rhodium (I) perchlorate

[Rh(cod)(L)]ClO$_4$ L=(S)-2,2'-bis[diphenylphosphino]-1,1'-binaphthyl

Under an argon atmosphere, to di-μ-chlorobis[($\eta^2$,$\eta^2$-1,5-cyclooctadiene)rhodium (I)] (310.5 mg, 0.630 mmoL) and silver perchlorate (267.5 mg, 1.290 mmoL) was added acetone (60 mL), and the mixture was stirred at room temperature for 1 hr. The insoluble material was removed by filtration, the filtrate was added to (S)-2,2'-bis[diphenylphosphino]-1,1'-binaphthyl ((S)-BINAP) (784.9 mg, 1.206 mmoL), and the mixture was stirred at room temperature for 1 hr. After the insoluble material was removed by filtration, the solvent was evaporated under reduced pressure. The residue was recrystallized from acetone and diethyl ether to give the title compound (0.65 g). yield 55%.

$^1$H-NMR (300 MHz, CD$_2$Cl$_2$, CD$_2$Cl$_2$) δ: 2.1-2.6(m, 8H), 4.6(m, 2H), 4.9(bs, 2H), 6.52(d, 2H), 6.7(t, 4H), 6.8(t, 2H), 7.0(t, 2H), 7.4(m, 6H), 7.55(m, 10H), 7.6-7.7(d, 2H), 7.7-7.8 (d, 2H), 7.8-7.9(m, 2H).

$^{31}$P-NMR (121 MHz, CD$_2$Cl$_2$, 85% H$_3$PO$_4$) δ: 25.2(s), 26.4(s).

Comparative Example 6

Asymmetric Isomerization of N,N-diethylnerylamine

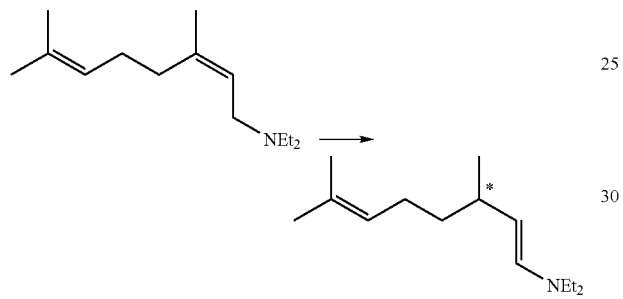

($\eta^2$,$\eta^2$-1,5-Cyclooctadiene){(S)-2,2'-bis[diphenylphosphino]-1,1'-binaphthyl}rhodium (I) perchlorate (27.0 mg, 0.0289 mmoL) synthesized in Reference Example 9 and N,N-diethylnerylamine (546.2 mg, 2.609 mmoL) were dissolved in tetrahydrofuran (5 mL), and the mixture was subjected to isomerization at 40° C. TOF (moL/moL·h, turnover frequency) was 78.1. The reaction mixture was analyzed by gas chromatography (column: Inert Cap CHIRAMIX, 0.32 mm×30 m) to find a conversion ratio of 100% and an optical purity of 100% ee(S).

Example 65

Asymmetric fluorination of tert-butyl 2-methyl-3-oxo-3-phenyl-propionate

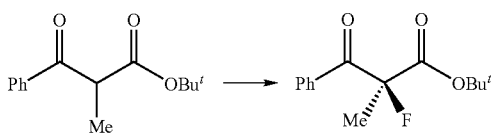

Under an argon atmosphere, {di-μ-hydroxobis[[(S)-2,2'-bis[bis(4-dimethylamino-3,5-dimethylphenyl)phosphino]-1,1'-binaphthyl]palladium (II)]}bistetrafluoroborate (22.4 mg, 0.01 mmoL) synthesized in Example 44, ethanol (0.3 mL), tert-butyl 2-methyl-3-oxo-3-phenyl-propionate (46.9 mg, 0.2 mmoL) and N-fluorobenzenesulfonimide (95 mg, 0.3 mmol) were stirred at room temperature for 48 hr. Saturated ammonium chloride solution (2 mL) was added to the mixture, and the mixture was extracted with ethyl acetate (20 mL). The organic layer was washed with water and saturated brine and concentrated under reduced pressure. The residue was purified using a silica gel column (ethyl acetate/n-hexane) to give the compound. By high performance liquid chromatography (column: CHIRALPAK AD-H, 4.6 mm×15 cm, n-hexane/2-propanol=200/1), the optical purity was 72.5% ee(S).

Reference Example 10

Synthesis of {di-μ-hydroxobis[[(S)-2,2'-bis(diphenylphosphino)-1,1'-binaphthyl]palladium (II)]} bistetrafluoroborate

[({Pd(L)}$_2$(μ-OH)$_2$](BF$_4$)$_2$ L=(S)-2,2'-bis(diphenylphosphino)-1,1'-binaphthyl Under an argon atmosphere, dichloro{(S)-2,2'-bis(diphenylphosphino)-1,1'-binaphthyl}palladium (II) (100 mg, 0.125 mmol) was stirred with dichloromethane (10 mL), water (1 mL), silver tetrafluoroborate (48 mg, 0.25 mmol, 2 equivalents) and molecular sieves 4A (1.5 g) at room temperature for 28 hr. The insoluble material was removed by filtration, and the solvent of the filtrate was evaporated to give the title compound (59 mg). yield 48.4%.

Comparative Example 7

Asymmetric fluorination of tert-butyl 2-methyl-3-oxo-3-phenyl-propionate

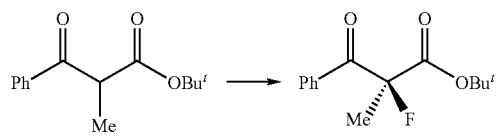

Under an argon atmosphere, {di-μ-hydroxobis[[(S)-2,2'-bis(diphenylphosphino)-1,1'-binaphthyl]palladium (II)]}bistetrafluoroborate (19.5 mg, 0.01 mmoL) synthesized in Reference Example 10, ethanol (0.3 mL), tert-butyl 2-methyl-3-oxo-3-phenyl-propionate (46.9 mg, 0.2 mmoL) and N-fluorobenzenesulfonimide (95 mg, 0.3 mmol) were stirred at room temperature for 48 hr. Saturated ammonium chloride solution (2 mL) was added to the mixture, and the mixture was extracted with ethyl acetate (20 mL). The organic layer was washed with water and saturated brine and concentrated under reduced pressure, and the residue was purified using a silica gel column (ethyl acetate/n-hexane) to give the compound. By high performance liquid chromatography (column: CHIRALPAK AD-H, 4.6 mm×15 cm, n-hexane/2-propanol=200/1), the optical purity was 58.1% ee(S).

Example 66

Synthesis of ($\eta^2$,$\eta^2$-1,5-cyclooctadiene){(S)-2,2'-bis[bis(4-dimethylamino-3,5-dimethylphenyl)phosphino]-1,1'-binaphthyl}nickel (0)

[Ni(cod)(L)]L=(S)-2,2'-bis[bis(4-dimethylamino-3, 5-dimethylphenyl)phosphino]-1,1'-binaphthyl Under an argon atmosphere, bis(1,5-cyclooctadiene)nickel (0) (48.3 mg, 0.1756 mmol) and (S)-2,2'-bis[bis(4-dimethylamino-3,5-dimethylphenyl)phosphino]-1,1'-binaphthyl (175.3 mg, 0.1932 mmol) were stirred in toluene (2 mL) at 60° C. for 10 min, and reacted at room temperature for 15 hr.

After filtration of the reaction mixture, the solvent was evaporated under reduced pressure to give the title compound (198.0 mg). Dark purple powder.

$^{31}$P-NMR (121 MHz, $C_6D_6$, 85% $H_3PO_4$): δ 30.6(s).

INDUSTRIAL APPLICABILITY

Using a transition metal complex having compound (II) of the present invention as a ligand for an asymmetric synthesis reaction (particularly, asymmetric reduction), the objective compound having an absolute configuration can be obtained efficiently.

This application is based on application No. 2005-272599 filed in Japan, the contents of which are incorporated hereinto by reference.

The invention claimed is:

1. A transition metal complex having, as a ligand, a compound represented by the formula

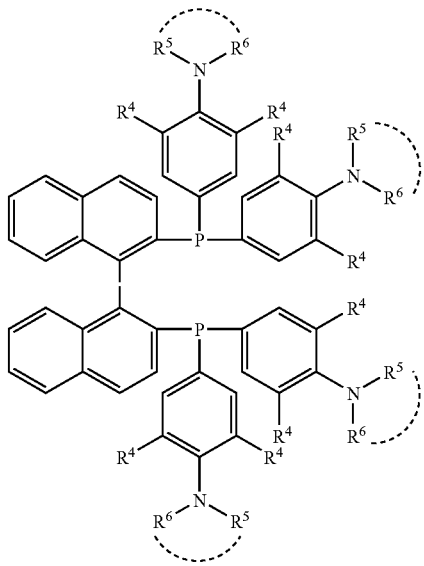

wherein $R^4$ is a $C_{1-6}$ alkyl group optionally having substituent(s), and $R^5$ and $R^6$ are each a $C_{1-6}$ alkyl group optionally having substituent(s), or $R^4$ is a hydrogen atom or a $C_{1-6}$ alkyl group optionally having substituent(s), and the formula

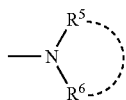

is a group represented by the formula

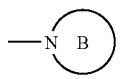

wherein ring B is a 3- to 8-membered ring optionally having substituent(s).

2. The transition metal complex of claim 1, wherein the transition metal is rhodium, ruthenium, iridium, palladium, nickel or copper.

3. The transition metal complex of claim 1, wherein the transition metal is rhodium, ruthenium or palladium.

4. The transition metal complex of claim 1, wherein $R^4$ is an unsubstituted $C_{1-6}$ alkyl group, and $R^5$ and $R^6$ are each an unsubstituted $C_{1-6}$ alkyl group.

5. The transition metal complex of claim 1, which is selected from the following:

(1) [Ru(OAc)$_2$(L)];
(2) [RuCl$_2$(L)(dmf)$_n$];
(3) [RuCl(Ar)(L)]Cl;
(4) [Ru(2-methylallyl)$_2$(L)];
(5) [RuCl$_2$(L)(X)];
(6) (NH$_2$Et$_2$)[{RuCl(L)}$_2$(μ-Cl)$_3$];
(7) [Rh(Y)(L)]Z;
(8) [PdCl$_2$(L)]; and
(9) [{Pd(L)}$_2$(μ-OH)$_2$]Z$_2$ wherein L is 2,2'-bis[bis(4-dimethylamino-3,5-dimethylphenyl)phosphino]-1,1'-binaphthyl, 2,2'-bis[bis(4-dimethylamino-3,5-diethylphenyl)phosphino]-1,1'-binaphthyl, 2,2'-bis[bis(4-dimethylamino-3,5-diisopropylphenyl)phosphino]-1,1'-binaphthyl, or 2,2'-bis[bis[4-(pyrrolidin-1-yl)phenyl]phosphino]-1,1'-binaphthyl, Ac is acetyl, dmf is N,N-dimethylformamide, n is an integer of not less than 1, Ar is benzene optionally having substituent(s), 2-methylallyl is η$^3$-2-methylallyl, X is ethylenediamine, 1,2-diphenylethylenediamine or 1,1-di(4-anisyl)-2-isopropyl-1,2-ethylenediamine, Y is 1,5-cyclooctadiene or norbornadiene, Z is a counter anion and trifluoromethanesulfonate, tetrafluoroborate, perchlorate, hexafluorophosphate or tetraphenylborate.

6. A catalyst comprising the transition metal complex of claim 1.

7. The transition metal complex of claim 1, wherein $R^4$ is a hydrogen atom or a $C_{1-6}$ alkyl group optionally having substituent(s), and the formula

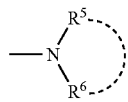

is a group represented by the formula

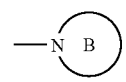

wherein ring B is a 3- to 8-membered ring optionally having substituent(s).

* * * * *